(12) United States Patent
Jensen et al.

(10) Patent No.: US 8,436,171 B2
(45) Date of Patent: May 7, 2013

(54) AMINO SUBSTITUTED PYRAZINES AS INHIBITORS OR PROTEIN KINASES

(75) Inventors: Annika Jenmalm Jensen, Uppsala (SE); Fredrik Lehmann, Uppsala (SE); Erik Nordling, Danderyd (SE); Vendela Parrow, Uppsala (SE)

(73) Assignee: Akinion Pharmaceuticals AB, Stockholm (SE)

( * ) Notice: Subject to any disclaimer, the term of this patent is extended or adjusted under 35 U.S.C. 154(b) by 124 days.

(21) Appl. No.: 12/865,359

(22) PCT Filed: Jan. 28, 2009

(86) PCT No.: PCT/EP2009/050931
§ 371 (c)(1),
(2), (4) Date: Dec. 17, 2010

(87) PCT Pub. No.: WO2009/095399
PCT Pub. Date: Aug. 6, 2009

(65) Prior Publication Data
US 2011/0098310 A1    Apr. 28, 2011

Related U.S. Application Data

(60) Provisional application No. 61/123,039, filed on Apr. 4, 2008.

(30) Foreign Application Priority Data

Feb. 1, 2008   (SE) ........................................ 0800250
May 21, 2008   (SE) ........................................ 0801185

(51) Int. Cl.
*C07D 241/20* (2006.01)
(52) U.S. Cl.
USPC ....................................................... 544/405
(58) Field of Classification Search ................... 544/405
See application file for complete search history.

(56) References Cited

U.S. PATENT DOCUMENTS

2006/0148824 A1    7/2006   Burns et al.

FOREIGN PATENT DOCUMENTS

| GB | 2 400 101 | 10/2004 |
| WO | 02/060492 | 8/2002 |
| WO | 2005/058876 | 6/2005 |
| WO | 2005/121126 | 12/2005 |
| WO | 2006/067466 | 6/2006 |
| WO | 2008/022164 | 2/2008 |
| WO | 2008/058341 | 5/2008 |

OTHER PUBLICATIONS

Advani, Anjali, "FLT3 and Acute Myelogenous Leukemia: Biology, Clinical Significance and Therapeutic Applicaitons", Current Pharmaceutical Design, 11:3449-3457, (2005).

Blume-Jensen et al., "Oncogenic Kinase Signalling", Nature, 411:355-365, (2001).
Cheng et al., "Tandutinib, an oral, small-molecule inhibitor of FLT3 for the treatment of AML and other cancer indications", IDrugs, 11(1):46-56, (2008).
Cui, Jingrong Jean, "Inhibitors targeting hepatocyte growth factor receptor and their potential therapeutic applications", Expert Opin. Ther. Patents, 17(9):1035-1045, (2007).
Furukawa et al., "Divergent cytotoxic effects of PKC412 in combination with conventional antileukemic agents in FLT3 mutation-positive versus -negative leukemia cell lines", Leukemia, 21:1005-1014, (2007).
Goodman et al., "The Pharmacological Basis of Therapeutics", McGraw Hill, Inc., eighth edition, copyright 1991, pp. 13-18.
Manning et al., "The Protein Kinase CoMplement of the Human Genome", Science, 298:1912-1934 (2002).
Martin et al., "PKCη as a therapeutic target in glioblastoma multiforme" Expert Opin. Ther. Targets 9(2):299-313, (2005).
Niculescu-Duvaz et al., "Novel Inhibitors of B-RAF Based on a Disubstituted Pyrazine Scaffold, Generation of a Nanomolar Lead", J. Med. Chem. 49:407-416, (2006).
Ostman, A., "Tyrosine kinase inhibitors: a brief review of the tumor biology, the drugs, and the clinical results", Helix Review Series, Oncology, 2:2-9, (2007).
Roboz et al., "Phase 1 study of PTK787/ZK 222584, a small molecule tyrosine kinase receptor inhibitor, for the treatment of acute myeloid leukemia and myelodysplastic syndrome", Leukemia, 20:952-957, (2006).
Rosnet et al., "Hematopoietic Receptors of Class III Receptor-Type Tyrosine Kinases", Critical Reviews in Oncogenesis, 4(6):595-613, (1993).
Silverman, Richard B., "The Organic Chemistry of Drug Design and Drug Action", Academic Press, Inc., copyright 1992, p. 352.

(Continued)

*Primary Examiner* — Brian McDowell
(74) *Attorney, Agent, or Firm* — White & Case LLP

(57) ABSTRACT

The present invention relates to compounds of the general formula (I) wherein $R^1$, $R^2$ and $R^3$ are as defined herein, which can act as inhibitors of protein kinases, specially the Fms-like tyrosine kinase 3 (FLT3). A species illustrative of members of the general formula is

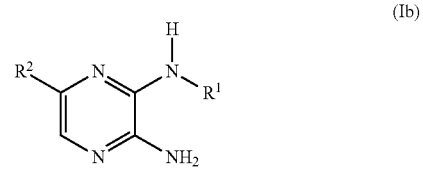

(Ib)

The invention also relates to the use of the compounds in therapy, pharmaceutical compositions comprising the compounds and the use of the compounds for the preparation of a medicament for the prophylaxis and treatment of hematological malignancies, such as AML, MLL, T-ALL, B-ALL and CMML, myeloproliferative disorders, other proliferative disorders like cancer, autoimmune disorders and skin disorders like psoriasis and atopic dermatitis.

2 Claims, No Drawings

OTHER PUBLICATIONS

[Retrieved from] SciFinder, American Chemical Society, CAS Registry No. 959570-50-4, Jul. 5, 2010, (4 pgs).

Tickenbrock et al., "Emerging Flt3 kinase inhibitors in the treatment of leukaemia", Expert Opin. Emerging Drugs, 11(1):153-165 (2006).

Weisel et al., "Effect of FLT3 Inhibition on Normal Hematopoietic Progenitor Cells", Ann. N. Y. Acad. Sci. 1106:190-196 (2007).

Eriksson, A. et al., "The novel tyrosine kinase inhibitor AKN-028 has significant antileukemic activity in cell lines and primary cultures of acute myeloid leukemia", Blood Cancer Journal (2012), 2, e.81, pp. 1-9.

AMINO SUBSTITUTED PYRAZINES AS INHIBITORS OR PROTEIN KINASES

CROSS-REFERENCE TO RELATED APPLICATIONS

This application is a National Stage application under 35 U.S.C. §371 and claims the benefit under 35 U.S.C. §119(a) of International Application No. PCT/EP2009/050931, having an International Filing Date of Jan. 28, 2009 which claims the benefit of priority of Sweden Application No. 0800250-3, having a filing date of Feb. 1, 2008, U.S. Provisional Application Ser. No. 61/123,039, having a filing date of Apr. 4, 2008, and Sweden Application Serial No. 0801185-0, having a filing date of May 21, 2008, all of which are incorporated herein in their entirety.

TECHNICAL FIELD

The present invention relates to pyrazine compounds that act as inhibitors of protein kinases, specially the Fms-like tyrosine kinase 3 (FLT3). The invention further relates to pharmaceutical compositions comprising these compounds, and to the use of the compounds for the preparation of a medicament for the treatment of hematological malignancies like AML, MLL, T-ALL, B-ALL and CMML, myeloproliferative disorders, other proliferative disorders like cancer, autoimmune disorders and skin disorders like psoriasis and atopic dermatitis.

BACKGROUND ART

Protein kinases are involved in the regulation of cellular metabolism, proliferation, differentiation and survival. Protein kinases phosphorylate proteins on serine/threonine or tyrosine residues. Activation of one class of kinase typically leads to activation of more than one signaling pathway through signaling crosstalk. The receptor tyrosine kinases (RTKs) are a major type of cell-surface receptors, where the intracellular part of the receptor has a kinase domain. The activating ligands are peptide/protein hormones, like the FL-ligand, Vascular Endothelial Growth factor (VEGF), Epidermal Growth factor (EGF), Fibroblast growth factor (FGF), nerve growth factor (NGF), platelet-derived growth factor (PDGF), insulin, etc. Binding of a ligand to the extracellular domain of an RTK results in receptor dimerisation and a conformational change that activates the kinase site on the intracellular domain. The kinase activity leads to a signal-transduction cascade by phosphorylation of other proteins that regulates cellular physiology and patterns of gene expression (for a review see Schlessinger, J. (2000) Cell 103: 211-225; and Blume-Jensen P. & Hunter T. (2001) Nature 411: 355-365). The intracellular signaling proteins activated in the signaling cascade can be other kinases and/or proteins involved in transcription and translation. There are several families of intracellular kinases. The Janus kinase (JAK) family of tyrosine kinases (JAK1, 2, 3, and Thy1) are activated through interaction with other proteins (see O'Shea, J. J. et al. (2002) Cell 109 (Suppl.) 121-131 and references therein). Serine/threonine kinases like the protein kinase C (PKC) family of isozymes and the mitogen activated kinases (MAP-kinase family) are also involved in the regulation of cell survival, proliferation and differentiation. The PKC-isozymes are activated by calcium, and diacylglycerol is an allosteric activator of some of the members of the PKC family (alpha beta gamma). Intracellular kinases interact with other proteins and are often translocated to other compartments upon activation (see Manning, G. et al. (2002) Science 298: 1912-1934; Martin. P. M. & Hussaini I. M. (2005) Expert Opin. Ther. Targets 9(2) 299-313 and references therein). Membrane association can be regulated by myristoylation, as in the case of PKC isozymes. Nuclear association has been described for several different classes of kinases. MAP-kinases are activated by other proteins and capable of translocating to the nucleus, where proteins involved in transcription and regulators of cell-cycle and differentiation becomes phosphorylated.

During normal development and differentiation both kinase activation and deactivation is tightly regulated. Oncogenic mutations, leading to constitutively active kinases, can trans-form normal cells to cancer cells. An activating mutation can be the result of a chromosome translocation giving rise to a fusion protein, for example as in chronic myeloic leukemia where the ABL-tyrosine kinase domain is fused to the BCR protein (for a review see Östman, A. (2007) Helix Review Series Oncology 2: 2-9; and Deininger, M. et al. (2005) Blood 105: 2640-2653).

During normal hematopoesis, FLT3 is active at the myeloblast stage, but the FLT3 activity is then switched off upon normal hematopoetic differentiation to mature blood cells (Gilliand, D. G. & Griffin, J. D. (2002) Blood 100: 1532-1542; Weisel, K. C. et al. (2007) Ann. N.Y. Acad. Sci. 1106: 190-196). In acute myeloic leukemia, (AML), the FLT3 expression is high in the majority of patients (70-90%) (Carow, C. E. et al. (1996) Blood 87 (3): 1089-1096; and Rosnet, O. et al (1993) Crit. Rev. Oncogenesis 4: 595-613). Furthermore, the FLT3 kinase activity is upregulated in one third of the patients due to an internal tandem duplication in the juxtamembrane position (FLT3-ITD), resulting in a ligand independent receptor dimerization and a constitutively active kinase. FLT3-ITD is a prognostic marker, with a statistically significant reduction in survival in the patient population harboring the mutation, specially if both alleles are affected. There are also activating point mutations (FLT3-PM) of FLT3 described in AML patients. These activating mutations can be found in the activation loop of the kinase domain (AL-mutations) or in the juxtamembrane domain (JM-mutations). For a review see Carow, C. E. et al. (1996) Blood 87 (3): 1089-1096; Tickenbrock, L. et al. (2006) Expert Opin. Emerging Drugs 11(1): 153-165; Anjali S. & Advani, A. S. (2005) Current Pharmaceutical Design 11: 3449-3457; Lee B. H. et al. (2007) Cancer Cell 12: 367-380); Stam, R. W. et al. (2005) Blood 106(7): 2484-2490; and references therein. In addition FLT3-ITD or FLT3-PM has been found in subsets of patients with other lymphoid or myeloid malignancies such as MLL, T-ALL and CMML, and a high FLT3-activity has been described in B-ALL (for a review see Lee, B. H. et al. (2007) Cancer Cell 12: 367-380.

However, FLT3 activity is part of the normal hematopoesis. If the proliferation of immature blast cells in the bone marrow is dysregulated, by an overstimulation of kinases like FLT3, this might result in a depletion of other hematopoetic cells. Blast cells then enter the bloodstream, instead of mature differentiated cells. The acute leukemic state results in anemia and neutropenia. Thus, blocking unfavorable kinase activity could reduce the proliferation of blast cells, and reduce the leukemic state. Several FLT3 kinase inhibitor has been tested in models of AML and in clinical indications where FLT3 is involved (Cheng, Y. & Paz, K. (2008) IDrugs 11(1): 46-56; Kiyoi, H. et al. (2007) Clin. Cancer Res. 13(15): 4575-4582; Roboz, G. J. et al. (2006) Leukemia 20: 952-957; Tse, K-F. et al. (2002) Leukemia 16: 2027-2036; Smith, B. D. et al. (2004) Blood 103: 3669-3676; Knapper, S. et al. (2006) Blood 108 (10): 3494-3503; and Furukawa, Y. et al. (2007)

Leukemia 21: 1005-1014). The AML cell-line MV4-11 carries the FLT3-ITD. This cell-line is very sensitive in viability/proliferation assays to inhibitors of FLT3 activity. However, in ex-vivo patient cells there is also crosstalk between the signaling pathways, molecules activated downstream of the FLT3 receptor can also be activated by other kinases. Knapper et al 2006 showed that even though the autophosphorylation of FLT3 was down-regulated in patient cells after exposure to FLT3 inhibitors, the phosphorylation state of the downstream effectors STAT and ERK were not diminished, possibly due to dysregulation of other signaling pathways apart from FLT3-phosphorylation.

The activity of FLT3 and other RTK is regulated by autophosphorylation and internalisation, the phosphorylation of the receptor is then removed by specific phosphatases that are also subject to regulation. A dysregulation of the internalization process and the dephosphorylation of the phosphatases could also have an impact on the RTK-activity and thus alter viability and proliferation of cells. As there are several orders of regulation, a kinase inhibitor needs to have a certain profile regarding its target specificity and mode of action to effectively inhibit proliferation and viability in cancer or a proliferative disorder.

DISCLOSURE OF THE INVENTION

This invention relates generally to certain pyrazine compounds that can act as inhibitors of the receptor tyrosine kinase FLT3 and related pharmaceutical compositions and methods.

While not wishing to be bound by theory, it is believed that the compounds described herein can be used, e.g., for the treatment or prevention of haematological malignancies, such as acute myeloic leukemia (AML); mixed lineage leukemia (MLL); T-cell type acute lymphocytic leukemia (T-ALL); B-cell type acute lymphocytic leukemia (B-ALL); chronic myelomonocytic leukemia (CMML); myeloproliferative disorders; other proliferative disorders, such as cancer; autoimmune disorders; and skin disorders, such as psoriasis and atopic dermatitis.

The compounds can further be used in conjunction with molecularly targeted agent, such as a conventional cytotoxic agent, or a compound used in postchemotherapy, stem-cell-directed maintenance therapy and in MLL-rearranged infant acute lymphoblastic leukaemia.

In a first aspect, this invention provides a compound of the Formula (I) and the geometrical isomers, racemates, tautomers and optical isomers thereof, as well as the pharmaceutically acceptable salts, hydrates, N-oxides and physiologically hydrolysable and acceptable esters and any prodrug forms thereof:

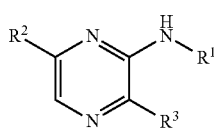

(I)

wherein:
$R^1$ is selected from a group consisting of:
(a) indolylethyl,
(b) cyclohexyl,
(c) hydroxycyclohexyl,
(d) 1,3-benzothiazolyl,
(e) $C_{1-3}$-alkyl-1,3-benzothiazolyl,
(f) benzothienyl,
(g) indolyl,
(h) indazolyl,
(i) $C_{1-3}$-alkylindolyl,
(j) carboxyindolyl,
(k) $C_{1-3}$-alkoxycarbonylindolyl,
(l) carbamoylindolyl,
(m) 4-methylpiperazin-1-ylcarbonylindolyl,
(n) carboxymethylindolyl,
(o) acetylaminophenyl, and
(p) $C_{1-3}$-alkylbenzimidazolyl;
$R^2$ is selected from a group consisting of:
(a) pyridinyl,
(b) fluoropyridinyl,
(c) chloropyridinyl,
(d) $C_{1-3}$-alkoxypyridinyl,
(e) thienyl,
(f) furyl,
(g) phenyl,
(h) fluorophenyl,
(i) hydroxyphenyl,
(j) cyanophenyl,
(k) hydroxymethylphenyl,
(l) aminophenyl,
(m) carbamoylphenyl,
(n) $C_{1-3}$-alkylaminocarbonylphenyl,
(o) dimethylaminocarbonylphenyl,
(p) ($C_{1-2}$-alkoxy-$C_{2-3}$-alkylaminocarbonyl)phenyl,
(q) (cyano-$C_{2-3}$-alkylaminocarbonyl)phenyl,
(r) (dimethylamino-$C_{2-3}$-alkylaminocarbonyl)phenyl,
(s) N-methoxy-N-methylaminocarbonylphenyl,
(t) morpholin-4-ylcarbonylphenyl,
(u) piperidin-1-ylcarbonylphenyl, and
(v) quinolinyl;
$R^3$ is hydrogen or $NH_2$;
with the proviso that the compound is not:
4-(6-{[2-(1H-indol-3-yl)ethyl]amino}pyrazin-2-yl)benzamide;
N'-(1H-indol-5-yl)-5-(quinolin-5-yl)pyrazine-2,3-diamine;
5-(3-aminophenyl)-N'-(1H-indol-5-yl)pyrazine-2,3-diamine;
3-[5-amino-6-(1H-indol-5-ylamino)pyrazinyl]phenol;
4-[5-amino-6-(1H-indol-5-ylamino)pyrazinyl]phenol; or
1-methyl-N-[6-(2-pyridinyl)pyrazinyl]-1H-benzimidazol-2-amine.

A preferred group of compounds of the invention are compounds of Formula (I) wherein $R^3$ is H, forming compounds of Formula (Ia):

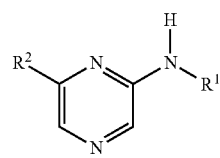

(Ia)

wherein:
$R^1$ is selected from a group consisting of:
(a) hydroxycyclohexyl,
(b) $C_{1-3}$-alkyl-1,3-benzothiazol-5-yl,
(c) 1,3-benzothiazolyl,
(d) benzothienyl,
(e) indolyl,
(f) $C_{1-3}$-alkylindol-5-yl,
(g) carboxylndolyl, (h) $C_{1-3}$-alkoxycarbonylindolyl; and $R^2$ is selected from a group consisting of:
(a) pyridinyl
(b) fluoro-pyridinyl and
(c) carbamoylphenyl A more preferred group of compounds of Formula (Ia) are those wherein
$R^1$ is selected from a group consisting of:
(a) 4-hydroxycyclohexyl,
(b) 2-methyl-1,3-benzothiazol-5-yl
(c) 1,3-benzothiazol-5-yl
(d) indol-5-yl and
(e) indol-6-yl and $R^2$ is selected from a group consisting of:
(a) 4-pyridinyl,
(b) 2-fluoro-4-pyridinyl and
(c) 4-carbamoylphenyl.

Preferred compounds of Formula (Ia) are:
N-(6-pyridin-4-ylpyrazin-2-yl)-1H-indol-5-amine,
N-[6-(2-fluoropyridin-4-yl)pyrazin-2-yl]-1H-indol-5-amine,
N-(6-pyridin-4-ylpyrazin-2-yl)-1H-indol-6-amine,
N-(6-pyridin-4-ylpyrazin-2-yl)-1,3-benzothiazol-5-amine,
2-methyl-N-(6-pyridin-4-ylpyrazin-2-yl)-1,3-benzothiazol-5-amine,
4-[6-(1H-indol-5-ylamino)pyrazin-2-yl]benzamide, and
4-{6-[(4-hydroxycyclohexyl)amino]pyrazin-2-yl}benzamide.

A preferred group of compounds of the invention are compounds of Formula (I) wherein $R^3$ is $NH_2$ forming compounds of Formula (Ib)

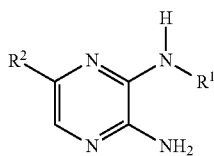

(Ib)

wherein:
$R^1$ is selected from a group consisting of:
(a) indolethyl,
(b) cyclohexyl,
(c) hydroxycyclohexyl,
(d) $C_{1-3}$-alkyl-1,3-benzothiazolyl,
(e) benzothienyl,
(f) indolyl,
(g) indazolyl,
(h) $C_{1-3}$-alkylindol-5-yl, and
(i) carbamoylindolyl;

$R^2$ is selected from a group consisting of:
(a) pyridinyl,
(b) chloropyridinyl,
(c) fluoropyridinyl,
(d) $C_{1-3}$-alkoxypyridinyl,
(e) thienyl,
(f) furyl,
(g) phenyl,
(h) fluorophenyl,
(i) hydroxyphenyl,
(j) cyanophenyl,
(k) hydroxymethylphenyl,
(l) aminophenyl,
(m) carbamoylphenyl,
(n) $C_{1-3}$-alkylaminocarbonylphenyl,
(o) dimethylaminocarbonylphenyl,
(p) ($C_{1-2}$-alkoxy-$C_{2-3}$-alkylaminocarbonyl)phenyl,
(q) cyano-$C_{2-3}$-alkylaminocarbonyl)phenyl,
(r) (dimethylamino-$C_{2-3}$-alkylaminocarbonyl)phenyl, and
(s) (N-methoxy-N-methylaminocarbonylphenyl
(t) (piperidin-1-ylcarbonyl)phenyl,
(u) (morpholin-4-ylcarbonyl)phenyl,
(v) quinolinyl.

A more preferred group of compounds of Formula (Ib) are those wherein
$R^1$ is selected from a group consisting of:
(a) 2-(indol-3-yl)ethyl
(b) 4-hydroxycyclohexyl,
(c) indol-5-yl,
(d) indol-4-yl,
(e) indazol-5-yl, and
(f) 2-methylindol-5-yl; and $R^2$ is selected from a group consisting of:
(a) 3-pyridinyl,
(b) 4-pyridinyl,
(c) 2-chloropyridin-4-yl,
(d) 3-thienyl,
(e) 3-furyl,
(f) 3-fluorophenyl,
(g) 3-hydroxyphenyl,
(h) 4-cyanophenyl,
(i) 4-aminophenyl,
(j) 4-carbamoylphenyl,
(k) 3-carbamoylphenyl,
(l) 4-dimethylaminocarbonylphenyl,
(m) 4-[(2-methoxyethyl)aminocarbonyl]phenyl, Preferred compounds of Formula (Ib) are:
N3-1H-indol-5-yl-5-pyridin-4-ylpyrazine-2,3-diamine,
N3-1H-indol-5-yl-5-pyridin-3-ylpyrazine-2,3-diamine,
5-(2-chloropyridin-4-yl)-N-3-1H-indol-5-ylpyrazine-2,3-diamine,
N3-(2-methyl-1H-indol-5-yl)-5-pyridin-4-ylpyrazine-2,3-diamine,
N3-(2-methyl-1H-indol-5-yl)-5-pyridin-3-ylpyrazine-2,3-diamine,
N3-1H-indol-4-yl-5-pyridin-4-ylpyrazine-2,3-diamine,
N3-1H-indol-5-yl-5-(3-thienyl)pyrazine-2,3-diamine,
5-(3-furyl)-N3-1H-indol-5-ylpyrazine-2,3-diamine,
N3-1H-indol-5-yl-5-phenylpyrazine-2,3-diamine,
5-(3-fluorophenyl)-N3-1H-indol-5-ylpyrazine-2,3-diamine,
3-[5-amino-6-(1H-indol-5-ylamino)pyrazin-2-yl]benzamide,
4-[5-amino-6-(1H-indol-5-ylamino)pyrazin-2-yl]benzamide,
4-{5-amino-6-[(2-methyl-1H-indol-5-yl)-amino]pyrazin-2-yl}benzamide,
4-[5-amino-6-(1H-indol-5-ylamino)pyrazin-2-yl]-N-(2-methoxyethyl)benzamide,
4-[5-amino-6-(1H-indol-5-ylamino)pyrazin-2-yl]-N-(2-cyanoethyl)benzamide,
4-[5-amino-6-(1H-indol-4-ylamino)pyrazin-2-yl]benzamide,
N3-[2-(1H-indol-3-yl)ethyl]-5-pyridin-4-ylpyrazine-2,3-diamine,
N3-[2-(1H-indol-3-yl)ethyl]-5-pyridin-3-ylpyrazine-2,3-diamine,
4-(5-amino-6-{[2-(1H-indol-3-yl)ethyl]amino}pyrazin-2-yl)benzamide,
4-(5-amino-6-{[2-(1H-indol-3-yl)ethyl]amino}pyrazin-2-yl)-N,N-dimethylbenzamide,
5-(4-aminophenyl)-N3-[2-(1H-indol-3-yl)ethyl]pyrazine-2,3-diamine, trans-4-[(3-amino-6-pyridin-4-ylpyrazin-2-yl)amino]cyclohexanol,
3-[5-amino-6-(1H-indol-5-ylamino)pyrazin-2-yl]phenol,
N3-1H-indazol-5-yl-5-pyridin-4-ylpyrazine-2,3-diamine,
4-[5-amino-6-(1H-indazol-5-ylamino)pyrazin-2-yl]-N-(2-methoxyethyl)benzamide, and
4-[5-amino-6-(1H-indazol-5-ylamino)pyrazin-2-yl]benzamide.

In one aspect, the present invention relates to a compound of Formula (I) for use in therapy, especially for use in the treatment or prophylaxis of a FLT3 related disorder. Examples of FLT3 related disorders include acute myeloic leukemia (AML); mixed lineage leukemia (MLL); T-cell type acute lymphocytic leukemia (T-ALL); B-cell type acute lymphocytic leukemia (B-ALL); chronic myelomonocytic leukemia (CMML). The present invention also relates to a compound of Formula (I) for use in the treatment or prophylaxis of hematological disorders related to dysregulated kinase activity such as myeloproliferative disorders; other proliferative disorders, such as cancer; autoimmune disorders; and skin disorders, such as psoriasis and atopic dermatitis.

In another aspect, the present invention relates to a pharmaceutical formulation comprising a compound of Formula (I) as active ingredient, in combination with a pharmaceutically acceptable diluent or carrier, especially for use in the treatment or prophylaxis of a FLT3 related disorder.

In one aspect, the present invention relates to a method for treating a human or animal subject suffering from a FLT3 related disorder. In a further aspect, the present invention relates to a method for treating a human or animal subject suffering from haematological malignancies such as acute myeloic leukemia (AML); mixed lineage leukemia (MLL); T-cell type acute lymphocytic leukemia (T-ALL); B-cell type acute lymphocytic leukemia (B-ALL); chronic myelomonocytic leukemia (CMML), and other hematological disorders like myeloproliferative disorders; other proliferative disorders, such as cancer; autoimmune disorders; and skin disorders, such as psoriasis and atopic dermatitis. The method can include administering to a subject (e.g., a human or an animal, dog, cat, horse, cow) in need thereof an effective amount of one or more compounds of Formula (I), their salts, or compositions containing the compounds or salts.

Methods delineated herein include those wherein the subject is identified as in need of a particular stated treatment. Identifying a subject in need of such treatment can be in the judgment of a subject or a health care professional and can be subjective (e.g. opinion) or objective (e.g. measurable by a test or diagnostic method).

In other aspects, the invention provides a method of treating a subject suffering from or susceptible to a FLT3 related disorder or disease, comprising administering to said subject in need thereof, an effective amount of a compound of Formula I or pharmaceutical composition thereof, such that said subject is treated for said disorder or disease.

In a further aspect, this invention relates to the use of a compound of formula (I) (e.g., as a medicament) for the treatment of a disease, disorder, or condition related to undesired activity of FLT3 kinase as described herein.

In another aspect, this invention relates to the use of a compound of formula (I) in the manufacture of a medicament containing a compound of formula I for the treatment of a disease, disorder, or condition related to undesired activity of FLT3 kinase as described herein.

One aspect of the present invention provides a pharmaceutical composition comprising an effective amount of a combination of an inhibitor of the receptor tyrosine kinase FLT3 according to formula (I) and another molecularly targeted agent, preferably a conventional cytotoxic agent, or a compound used in postchemotherapy, stem-cell-directed maintenance therapy and in MLL-rearranged infant acute lymphoblastic leukaemia; and optionally a pharmaceutically acceptable carrier.

Another aspect of the invention provides a method of preventing or treating haematological malignancies, myeloproliferative disorder, other proliferative disorders, autoimmune disorders and skin disorders, comprising administering to a human or animal subject in need thereof an inhibitor of the receptor tyrosine kinase FLT3 according to formula (I) simultaneously or sequentially with another molecularly targeted agent, preferably a conventional cytotoxic agent, or a compound used in postchemotherapy, stem-cell-directed maintenance therapy and in MLL-rearranged infant acute lymphoblastic leukaemia; in sufficient amounts to provide a therapeutic effect.

Still another aspect of the invention provides the use of an inhibitor of the receptor tyrosine kinase FLT3 according to formula (I) together with another molecularly targeted agent, such as a conventional cytotoxic agent, or a compound used in postchemotherapy, stem-cell-directed maintenance therapy and in MLL-rearranged infant acute lymphoblastic leukaemia; for the manufacture of a medicament for the treatment of haematological malignancies, myeloproliferative disorder, other proliferative disorders, autoimmune disorders and skin disorders.

Another aspect of the invention provides a process for preparing a pharmaceutical composition, wherein an inhibitor of the receptor tyrosine kinase FLT3 according to formula (I) and another molecularly targeted agent, such as a conventional cytotoxic agent, or a compound used in postchemotherapy, stem-cell-directed maintenance therapy and in MLL-rearranged infant acute lymphoblastic leukaemia; in a combined therapeutic amount are intimately mixed with a pharmaceutically acceptable carrier.

Yet another aspect of the invention provides a product containing an inhibitor of the receptor tyrosine kinase FLT3 according to formula (I) further comprising another molecularly targeted agent, such as a conventional cytotoxic agent, or a compound used in post-chemotherapy, stem-cell-directed maintenance therapy and in MLL-rearranged infant acute lymphoblastic leukaemia; as a combined preparation for simultaneous, separate or sequential use in therapy of haematological malignancies, myeloproliferative disorder, other proliferative disorders, autoimmune disorders and skin disorders.

Another aspect of the present invention is a process for the preparation of a compound according to formula (I) of the invention comprising reacting 2-amino-3,5-dibromo-pyrazin and the appropriate amine followed by a Suzuki coupling. More specifically, the process for the preparation of a compound according to formula (I) of the invention comprising one or more of the following steps: 2-amino-3,5-dibromo-pyrazin (3 equiv) and the appropriate amine is dissolved in 4 mL water and the resulting mixture heated to 195° C. for 1 hour. Water and ethyl acetate is added and the phases separated. The water phase is extracted once more with ethyl acetate. The combined organic phases is washed (water and brine) and concentrated to yield a crude mixture of product and unreacted amine or alcohol. This crude mixture is used without further purification or characterization in the subsequent Suzuki reaction which is performed according to typical Suzuki protocols published in the literature.

The chemicals used in the synthetic routes delineated herein may include, for example, solvents, reagents, catalysts, and protecting group and deprotecting group reagents.

The methods described above may also additionally include steps, either before or after the steps described specifically herein, to add or remove suitable protecting groups in order to ultimately allow synthesis of the compounds. In addition, various synthetic steps may be performed in an alternate sequence or order to give the desired compounds. Synthetic chemistry transformations useful in synthesizing applicable compounds are known in the art and include, for example, those described in R. Larock, *Comprehensive Organic Transformations*, VCH Publishers (1989); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995) and subsequent editions thereof.

Methods for carrying out the reactions described above are well known to those skilled in the art. The necessary starting materials for preparing the compounds of formula (I) are either known or may be prepared in analogy with the preparation of known compounds. The compounds of formula (I) may possess one or more chiral carbon atoms, and they may therefore be obtained in the form of optical isomers, e.g. as a pure enantiomer, or as a mixture of enantiomers (racemate) or as a mixture containing diastereomers. The separation of mixtures of optical isomers to obtain pure enantiomers is well known in the art and may, for example, be achieved by fractional crystallization of salts with optically active (chiral) acids or by chromatographic separation on chiral columns. All isomeric forms possible (pure enantiomers, diastereomers, tautomers, racemic mixtures and unequal mixtures of two enantiomers) for the compounds delineated are within the scope of the invention. When the compounds described herein contain olefinic double bonds of geometric asymmetry, it is intended to include both trans and cis (E and Z) geometric isomers.

The compounds of the formula (I) may be used as such or, where appropriate, as pharmacologically acceptable salts (acid or base addition salts) thereof. The pharmacologically acceptable addition salts mentioned above are meant to comprise the therapeutically active non-toxic acid and base addition salt forms that the compounds are able to form. Compounds that have basic properties can be converted to their pharmaceutically acceptable acid addition salts by treating the base form with an appropriate acid. Exemplary acids include inorganic acids, such as hydrogen chloride, hydrogen bromide, hydrogen iodide, sulphuric acid, phosphoric acid; and organic acids such as formic acid, acetic acid, propanoic acid, hydroxyacetic acid, lactic acid, pyruvic acid, glycolic acid, maleic acid, malonic acid, oxalic acid, benzenesulphonic acid, toluenesulphonic acid, methanesulphonic acid, trifluoroacetic acid, fumaric acid, succinic acid, malic acid, tartaric acid, citric acid, salicylic acid, p-aminosalicylic acid, pamoic acid, benzoic acid, ascorbic acid and the like. Exemplary base addition salt forms are the sodium, potassium, calcium salts, and salts with pharmaceutically acceptable amines such as, for example, ammonia, alkylamines, benzathine, and amino acids, such as, e.g. arginine and lysine. The term addition salt as used herein also comprises solvates which the compounds and salts thereof are able to form, such as, for example, hydrates, alcoholates and the like.

For clinical use, the compounds of the invention are formulated into pharmaceutical formulations for oral, rectal, parenteral or other mode of administration. Pharmaceutical formulations are usually prepared by mixing the active substance, or a pharmaceutically acceptable salt thereof, with conventional pharmaceutical excipients. Examples of excipients are water, gelatin, gum arabicum, lactose, microcrystalline cellulose, starch, sodium starch glycolate, calcium hydrogen phosphate, magnesium stearate, talcum, colloidal silicon dioxide, and the like. Such formulations may also contain other pharmacologically active agents, and conventional additives, such as stabilizers, wetting agents, emulsifiers, flavouring agents, buffers, and the like. Usually, the amount of active compounds is between 0.1-95% by weight of the preparation, preferably between 0.2-20% by weight in preparations for parenteral use and more preferably between 1-50% by weight in preparations for oral administration.

The formulations can be further prepared by known methods such as granulation, compression, microencapsulation, spray coating, etc. The formulations may be prepared by conventional methods in the dosage form of tablets, capsules, granules, powders, syrups, suspensions, suppositories or injections. Liquid formulations may be prepared by dissolving or suspending the active substance in water or other suitable vehicles. Tablets and granules may be coated in a conventional manner.

The dose level and frequency of dosage of the specific compound will vary depending on a variety of factors including the potency of the specific compound employed, the metabolic stability and length of action of that compound, the patient's age, body weight, general health, sex, diet, mode and time of administration, rate of excretion, drug combination, the severity of the condition to be treated, and the patient undergoing therapy. The daily dosage may, for example, range from about 0.001 mg to about 100 mg per kilo of body weight, administered singly or multiply in doses, e.g. from about 0.01 mg to about 1000 mg each. Normally, such a dosage is given orally but parenteral administration may also be chosen.

DEFINITIONS

The following definitions shall apply throughout the specification and the appended claims.

The terms "FLT3 related disorder", and "disorder or condition related to undesired activity of FLT3", have been used interchangeably herein to denote any disorder or symptom wherein the FLT3 is involved in the process or presentation of the disorder or the symptom. The FLT3 related disorders thus e.g. include, but are not limited to, haematological malignancies, such as acute myeloic leukemia (AML); mixed lineage leukemia (MLL); T-cell type acute lymphocytic leukemia (T-ALL); B-cell type acute lymphocytic leukemia (B-ALL) and chronic myelomonocytic leukemia (CMML).

Unless otherwise stated or indicated, the term "$C_{1-6}$-alkyl" denotes a straight or branched alkyl group having from 1 to 6 carbon atoms. Examples of said $C_{1-6}$-alkyl include methyl, ethyl, n-propyl, iso-propyl, n-butyl, iso-butyl, sec-butyl, t-butyl and straight- and branched-chain pentyl and hexyl. For parts of the range "$C_{1-6}$-alkyl" all subgroups thereof are contemplated such as $C_{1-5}$-alkyl, $C_{1-4}$-alkyl, $C_{1-3}$-alkyl, $C_{1-2}$-alkyl, $C_{2-6}$-alkyl, $C_{2-5}$-alkyl, $C_{2-4}$-alkyl, $C_{2-3}$-alkyl, $C_{3-6}$-alkyl, $C_{4-5}$-alkyl, etc. Likewise, "aryl-$C_{1-6}$-alkyl" means a $C_{1-6}$-alkyl group substituted by an aryl group. Examples include benzyl, 2-phenylethyl, 1-phenylethyl and 1-naphthylmethyl.

Unless otherwise stated or indicated, the term "$C_{1-3}$-alkoxy" denotes a straight or branched alkoxy group having from 1 to 3 carbon atoms. Examples of said $C_{1-3}$-alkoxy include methoxy, ethoxy, n-propoxy, iso-propoxy. For parts of the range "$C_{1-3}$-alkoxy" all subgroups thereof are contemplated such as $C_{1-2}$-alkoxy and $C_{2-3}$-alkoxy.

Unless otherwise stated or indicated, the term "$C_{1-3}$-alkoxy-carbonyl" denotes a straight or branched alkoxy group having from 1 to 3 carbon atoms connected to an carbonyl group. Examples of said $C_{1-3}$-alkoxy-carbonyl include methoxycarbonyl, ethoxycarbonyl, iso-propoxycarbonyl. For parts of the range "$C_{1-3}$-alkoxy-carbonyl" all subgroups thereof are contemplated such as $C_{1-2}$-alkoxy-carbonyl and $C_{2-3}$-alkoxycarbonyl.

"Pharmaceutically acceptable" means being useful in preparing a pharmaceutical composition that is generally safe, non-toxic and neither biologically nor otherwise undesirable and includes being useful for veterinary use as well as human pharmaceutical use.

"Treatment" as used herein includes prophylaxis of the named disorder or condition, or amelioration or elimination of the disorder once it has been established.

"An effective amount" refers to an amount of a compound that confers a therapeutic effect on the treated subject. The therapeutic effect may be objective (i.e., measurable by some test or marker) or subjective (i.e., subject gives an indication of or feels an effect). The term "prodrug forms" means a pharmacologically acceptable derivative, such as an ester or an amide, which derivative is biotransformed in the body to form the active drug. Reference is made to Goodman and Gilman's, The Pharmacological basis of Therapeutics, $8^{th}$ ed., Mc-Graw-Hill, Int. Ed. 1992, "Biotransformation of Drugs", p. 13-15; and "The Organic Chemistry of Drug Design and Drug Action" by Richard B. Silverman. Chapter 8, p 352. (Academic Press, Inc. 1992. ISBN 0-12-643730-0).

Combinations of substituents and variables envisioned by this invention are only those that result in the formation of stable compounds. The term "stable" as used herein, refers to compounds which possess stability sufficient to allow manufacture and which maintains the integrity of the compound for a sufficient period of time to be useful for the purposes detailed herein (e.g., therapeutic administration to a subject for the treatment of a FLT3 related disorder or disease (including those delineated herein), e.g. haematological malignancies, such as acute myeloic leukemia (AML); mixed lineage leukemia (MLL); T-cell type acute lymphocytic leukemia (T-ALL); B-cell type acute lymphocytic leukemia (B-ALL) and chronic myelomonocytic leukemia (CMML)).

The recitation of a listing of chemical groups in any definition of a variable herein includes definitions of that variable as any single group or combination of listed groups. The recitation of an embodiment for a variable herein includes that embodiment as any single embodiment or in combination with any other embodiments or portions thereof.

The invention will now be further illustrated by the following non-limiting Examples. The specific examples below are to be construed as merely illustrative, and not limitative of the remainder of the disclosure in any way whatsoever. Without further elaboration, it is believed that one skilled in the art can, based on the description herein, utilize the present invention to its fullest extent. All publications cited herein are hereby incorporated by reference in their entirety.

The structures depicted herein, may contain certain —NH—, —NH$_2$ (amino) and —OH (hydroxyl) groups where the corresponding hydrogen atom(s) do not explicitly appear; however they are to be read as —NH—, —NH$_2$ or —OH as the case may be.

Methods $^1$H Nuclear magnetic resonance (NMR) and $^{13}$C NMR were recorded on a Bruker Advance DPX 400 spectrometer at 400.1 MHz and 100.6 MHz, respectively. All spectra were recorded using residual solvent or tetramethylsilane (TMS) as internal standard.

Low-resolution electrospray ionization mass spectra (LRESIMS) were obtained using an Agilent MSD mass spectrometer or a Waters ZQ mass spectrometer. High-resolution electrospray ionization mass spectra (HRESIMS) were obtained on an Agilent LC/MSD TOF connected to an Agilent 1100 LC-system, Ion Source: ESI, Ion polarity: pos, Data: profile mode, Scan range: 100-1100 Da, MS parameters: Fragmentor 215V, Skimmer 560V och OCT RF (octpole rods) 250 V.; Reference Masses 121.050873 and 922.009798 (Agilent reference Mix); LC: A 15 mM ammonium acetate; B 100 MeCN; flow 400 µL/min isocratic. Flash chromatography was performed on Merck silica gel 60 (230-400 mesh). Microwave irradiations were carried out using the Smith Creator or Optimizer (Personal Chemistry) using 0.5-2 mL or 2-5 mL Smith Process vials fitted with aluminum caps and septa. The compounds were automatically named using ACD/NAME 6.0 (Advanced Chemistry Development, Inc., Toronto, Canada).

Analytical LCMS data were obtained with:

System A: Agilent MSD mass spectrometer; Agilent 1100 system; ACE 3 C8 column (50×3.0 mm); Water containing 0.1% TFA and acetonitrile were used as mobile phases at a flow rate of 1 mL/min with gradient times of 3.0 min (gradient 10-97% acetonitrile); or System B: Agilent MSD mass spectrometer; Agilent 1100 system; YMC ODS-AQ column (33×3.0 mm); Water containing 0.1% TFA and acetonitrile were used as mobile phases at a flow rate of 1 mL/min with gradient times of 3.0 min (gradient 10-97% acetonitrile); or System C: Waters ZQ mass spectrometer; Waters 996 PDA detector (DAD 215-395 nm); ACE C8 (3 µm) column (30×3.0 mm) (from ACT); Water containing 10 mM ammonium acetate (pH=7) and acetonitrile were used as mobile phases at a flow rate of 1 mL/min with gradient times of 3.2 min (gradient 5-100% acetonitrile).

Preparative HPLC was performed on Gilson system equipped with:

System D: ACE C8 5 µm (21.2×50 mm) column. Water containing 0.1% TFA and acetonitrile were used as mobile phases at a flow rate of 25 mL/min with gradient times of 6 min.; or System E: XTerra Prep MS C18 5 µm (19×50 mm) column. Water containing 50 mM NH$_4$HCO$_3$ (pH=10) and acetonitrile were used as mobile phases at a flow rate of 25 mL/min with gradient times of 6 min; or Xterra MS C18 5 µm (30×100 mm) column.

Water containing 50 mM NH$_4$HCO$_3$ (pH=10) and acetonitrile were used as mobile phases at a flow rate of 40 mL/min with gradient times of 8.5 min; or System F: YMC ODS-AQ 10 µM (30×150 mm) column. Water containing 0.1% TFA and acetonitrile were used as mobile phases at a flow rate of 45 mL/min with gradient times of 8.5 min.

The following abbreviations have been used:

DMSO means dimethyl sulphoxide,

HPLC means high performance liquid chromatography,

TFA means trifluoroacetic acid.

HRMS means high resolution mass spectrometry

EXAMPLES

Procedure A

General Procedure for $S_NAr$ on 2-amino-3,5-dibromo-pyrazine

2-Amino-3,5-dibromo-pyrazine, triethylamine (3 equiv) and the appropriate amine or alcohol (3 equiv) were dissolved in 4 mL water and the resulting mixture was heated to 195° C. for 1 hour. Water and ethyl acetate were added and the phases separated. The water phase was extracted once more with ethyl acetate. The combined organic phases were washed (water and brine) and concentrated to yield a crude mixture of product and unreacted amine or alcohol. This crude mixture was used without further purification or characterization in the subsequent Suzuki reaction.

Procedure B

General Procedure for Suzuki Coupling

A mixture of the pyrazinyl bromide from procedure A (1 equiv), the appropriate boronic acid (1 equiv), $K_2CO_3$ (3 equiv) and $Pd(dppf)Cl_2*CH_2Cl_2$ (0.1 equiv) in 4 mL dioxane/water (4:1) was heated to 150° C. for 15 min. The mixture was filtered through a small plug of silica and concentrated. The crude product was purified by preparative HPLC (ACE C8 column; mobile phase: 0.1% $TFA-CH_3CN$) to give the title compound as a white solid in the form of its corresponding trifluoroacetate salt.

Intermediate 1

5-Bromo-N-3-1H-indol-5-yl-pyrazine-2,3-diamine

Using procedure A: 2-Amino-3,5-dibromo-pyrazine (100 mg) and 5-aminoindole (200 mg) yielded 150 mg of a 1:1 mixture of 5-aminoindole and the desired product MS m/z 303 [M+H]$^+$ which was used without further purification or characterization.

Example 1

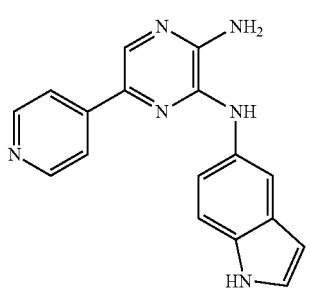 [SMILES: Nc1ncc(-c2ccncc2)nc1Nc1ccc2[nH]ccc2c1]

N3-1H-Indol-5-yl-5-pyridin-4-ylpyrazine-2,3-diamine, trifluoroacetate

Using procedure B: 5-Bromo-N3-1H-indol-5-yl-pyrazine-2,3-diamine (20 mg) and 4-pyridyl-boronic acid (12 mg) yielded 1.7 mg of the title compound. MS m/z 303 [M+H]$^+$. $^1$H NMR (400 MHz, $CD_3OD$) δ ppm 6.48 (d, J=3.01 Hz, 1H) 7.26-7.33 (m, 1H) 7.33-7.50 (m, 2H) 7.92 (d, J=1.25 Hz, 1H) 8.37 (s, 1H) 8.45 (d, J=7.03 Hz, 2H) 8.64 (d, J=7.03 Hz, 2H).

Example 2

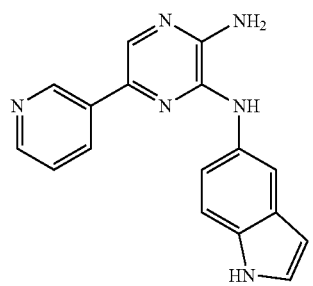 [SMILES: Nc1ncc(-c2cccnc2)nc1Nc1ccc2[nH]ccc2c1]

N3-1H-Indol-5-yl-5-pyridin-3-ylpyrazine-2,3-diamine, trifluoroacetate

Using procedure B: 5-Bromo-N3-1H-indol-5-yl-pyrazine-2,3-diamine (20 mg) and 3-pyridyl-boronic acid (12 mg) yielded 1.3 mg of the title compound. HRMS calcd for $C_{17}H_{14}N_6$: 302.1280. Found: 302.1279. $^1$H NMR (400 MHz, $CD_3OD$): 6.49 (d, 1H, J=4 Hz), 7.29-7.46 (m, 3H), 7.88-7.94 (m, 2H), 8.02 (s, 1H), 8.64 (d, 1H, J=8 Hz), 8.84 (d, 1H, J=8 Hz), 9.19 (s, 1H).

Example 3

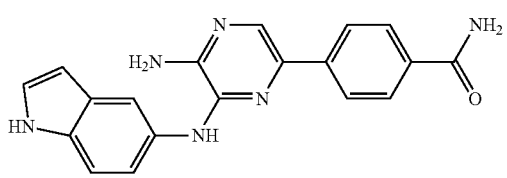 [SMILES: NC(=O)c1ccc(-c2cnc(N)c(Nc3ccc4[nH]ccc4c3)n2)cc1]

4-[5-Amino-6-(1H-indol-5-ylamino)pyrazin-2-yl]benzamide, trifluoroacetate

Using procedure B: 5-Bromo-N3-1H-indol-5-yl-pyrazine-2,3-diamine (20 mg) and 4-benzamide boronic acid (16 mg) yielded 0.9 mg of the title compound. HRMS calcd for $C_{19}K_6N_6O$: 344.1386. Found: 344.1381. $^1$H NMR (400 MHz, $CD_3OD$): δ 6.49 (d, 1H, J=4 Hz), 7.30 (d, 1H, J=4 Hz), 7.42-7.47 (m, 2H), 7.81 (s, 1H), 7.94 (d, 2H, J=8 Hz), 8.01-8.06 (m, 3H).

Example 4

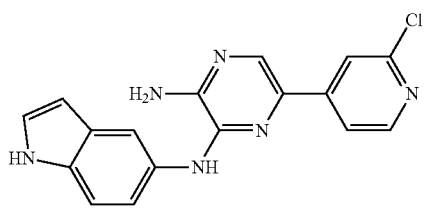 [SMILES: Nc1ncc(-c2ccnc(Cl)c2)nc1Nc1ccc2[nH]ccc2c1]

5-(2-Chloropyridin-4-yl)-N3-1H-indol-5-ylpyrazine-2,3-diamine, trifluoroacetate

Using procedure B: 5-Bromo-N3-1H-indol-5-yl-pyrazine-2,3-diamine (20 mg) and 2-chloropyridin-4-yl boronic acid (20 mg) yielded 4.0 mg of the title compound.

Example 5

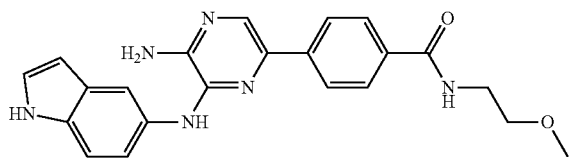 [SMILES: COCCNC(=O)c1ccc(-c2cnc(N)c(Nc3ccc4[nH]ccc4c3)n2)cc1]

4-[5-Amino-6-(1H-indol-5-ylamino)pyrazin-2-yl]-N-(2-methoxyethyl)benzamide, trifluoroacetate Using procedure B: 5-Bromo-N3-1H-indol-5-yl-pyrazine-2,3-diamine (25 mg) and [4-[[(2-methoxyethyl)amino]carbonyl]phenyl]boronic acid (27 mg) yielded 4.2 mg of the title compound. MS m/z 403 [M+H]$^+$.

Example 6

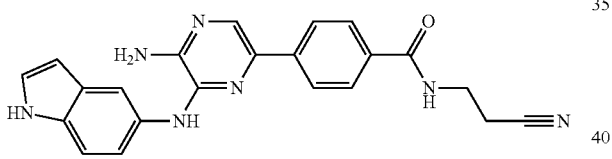

4-[5-Amino-6-(1H-indol-5-ylamino)pyrazin-2-yl]-N-(2-cyanoethyl)benzamide, trifluoroacetate Using procedure B: 5-Bromo-N3-1H-indol-5-yl-pyrazine-2,3-diamine (25 mg) and [4-(2-cyanoethylaminocarbonyl)phenyl]boronic acid (27 mg) yielded 3.2 mg of the title compound. MS m/z 398 [M+H]$^+$. $^1$H NMR (500 MHz, DMSO-d$_6$) δ ppm 2.78 (t, J=6.70 Hz, 2H) 3.51 (q, J=6.09 Hz, 2H) 6.42 (s, 1H) 7.27-7.47 (m, 3H) 7.76-8.18 (m, 6H) 8.38 (s, 1H) 8.63-9.11 (m, 1H) 10.98 (s, 1H).

Intermediate 2

5-Bromo-N3-1H-indol-4-yl-pyrazine-2,3-diamine

Using procedure A: 2-Amino-3,5-dibromo-pyrazine (300 mg) and 4-aminoindole (470 mg) yielded 700 mg of a 1:1 mixture of 4-aminoindole and the desired product MS m/z 303 [M+H]$^+$ which was used without further purification or characterization.

Example 7

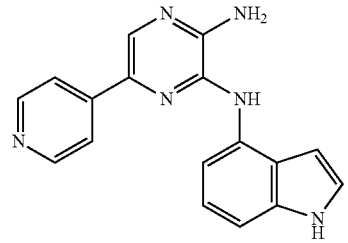 [SMILES: Nc1ncc(-c2ccncc2)nc1Nc1cccc2[nH]ccc12]

N3-1H-Indol-4-yl-5-pyridin-4-ylpyrazine-2,3-diamine, trifluoroacetate

Using procedure B: 5-Bromo-N3-1H-indol-4-yl-pyrazine-2,3-diamine (25 mg) and 4-pyridinyl boronic acid (15 mg) yielded 1.2 mg of the title compound. HRMS calcd for C$_{17}$H$_{14}$N$_6$: 302.1280. Found: 302.1278. $^1$H NMR (400 MHz, CD$_3$OD) ppm 6.41 (d, J=3 Hz, 1H) 7.19 (d, J=7 Hz, 1H) 7.21-7.32 (m, 2H) 7.38 (d, J=7 Hz, 1H) 8.33 (d, J=6 Hz, 2H) 8.44 (s, 1H) 8.57 (d, J=6 Hz, 2H).

Example 8

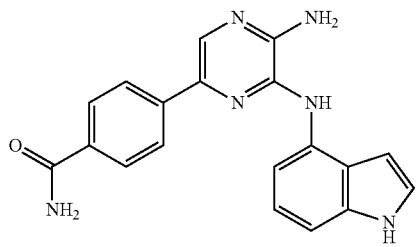 [SMILES: NC(=O)c1ccc(-c2cnc(N)c(Nc3cccc4[nH]ccc34)n2)cc1]

4-[5-Amino-6-(1H-indol-4-ylamino)pyrazin-2-yl]benzamide, trifluoroacetate

Using procedure B: 5-Bromo-N3-1H-indol-4-yl-pyrazine-2,3-diamine (25 mg) and 4-benzamide boronic acid (20 mg) yielded 1.1 mg of the title compound. HRMS calcd for C$_{19}$H$_{16}$N6O: 344.1386. Found: 344.1384. $^1$H NMR (400 MHz, CD$_3$OD) δ 6.50 (d, J=2 Hz, 1H) 7.20 (t, J=7 Hz, 1H) 7.28 (d, J=3 Hz, 1H) 7.33 (d, J=8 Hz, 1H) 7.49 (d, J=7 Hz, 1H) 7.82-7.96 (m, 5H).

Intermediate 3

5-Bromo-N3-(2-methyl-1H-indol-5-yl)-pyrazine-2,3-diamine

Using procedure A: 2-Amino-3,5-dibromo-pyrazine (300 mg) and 5-amino-2-methyl-indole (520 mg) yielded 400 mg of a 1:1 mixture of and 5-amino-2-methyl-indole and the desired product MS m/z 319 [M+H]$^+$ which was used without further purification or characterization.

Example 9

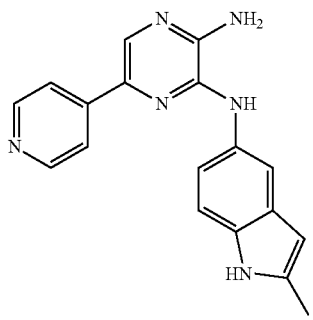 [SMILES: Cc1cc2cc(Nc3nc(-c4ccncc4)cnc3N)ccc2[nH]1]

N3-(2-Methyl-1H-indol-5-yl)-5-pyridin-4-ylpyrazine-2,3-diamine, trifluoroacetate Using procedure B: 5-Bromo-N3-(2-methyl-1H-indol-5-yl)-pyrazine-2,3-diamine (26 mg) and 4-pyridinyl boronic acid (14 mg) yielded 3.0 mg of the title compound. HRMS calcd for $C_{18}H_{16}N_6$: 316.1436. Found: 316.1437. $^1$H NMR (400 MHz, CD$_3$OD) δ ppm 2.45 (s, 3H) 7.16-7.47 (m, 3H) 7.76 (s, 1H) 8.35 (s, 1H) 8.45 (d, J=6 Hz, 2H) 8.65 (d, J=6 Hz, 2H).

Example 10

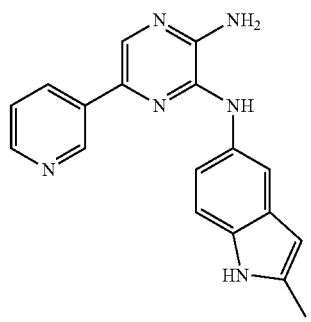 [SMILES: Cc1cc2cc(Nc3nc(-c4cccnc4)cnc3N)ccc2[nH]1]

N3-(2-Methyl-1H-indol-5-yl)-5-pyridin-3-ylpyrazine-2,3-diamine, trifluoroacetate Using procedure B: 5-Bromo-N3-(2-methyl-1H-indol-5-yl)-pyrazine-2,3-diamine (26 mg) and 3-pyridinyl boronic acid (14 mg) yielded 3.4 mg of the title compound. HRMS calcd for $C_{18}H_{16}N_6$: 316.1436. Found: 316.1434.

Example 11

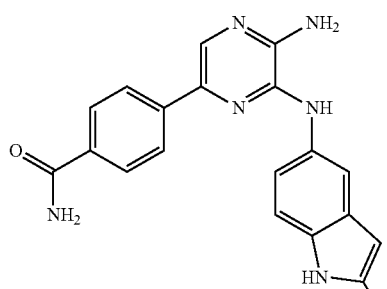

4-{5-Amino-6-[(2-methyl-1H-indol-5-yl)amino]pyrazin-2-yl}benzamide, trifluoroacetate Using procedure B: 5-Bromo-N3-(2-methyl-1H-indol-5-yl)-pyrazine-2,3-diamine (26 mg) and 4-benzamide boronic acid (19 mg) yielded 2.2 mg of the title compound. HRMS calcd for $C_{20}H_{18}N_6O$: 358.1542. Found: 358.1542. $^1$H NMR (400 MHz, CD$_3$OD) δ 2.46 (s, 3H) 7.15-7.48 (m, 3H) 7.77 (s, 1H) 7.90 (s, 1H) 7.91-7.96 (m, 2H) 8.00-8.12 (m, 2H).

Intermediate 4

5-Bromo-N3-(1H-indazol-5-yl)-pyrazine-2,3-diamine

Using procedure A: 2-Amino-3,5-dibromo-pyrazine (300 mg) and 5-amino-indazole (470 mg) yielded 320 mg of a 1:3 mixture of 5-amino-indazole and the desired product MS m/z 306 [M+H]$^+$ which was used without further purification or characterization.

Example 12

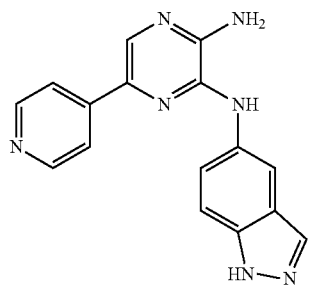 [SMILES: Nc1ncc(-c2ccncc2)nc1Nc1ccc2[nH]ncc2c1]

N3-1H-Indazol-5-yl-5-pyridin-4-ylpyrazine-2,3-diamine, trifluoroacetate

Using procedure B: 5-Bromo-N3-(1H-indazol-5-yl)-pyrazine-2,3-diamine (15 mg) and 4-pyridyl boronic acid (9 mg) yielded 1.3 mg of the title compound. HRMS calcd for $C_{16}H_{13}N_7$: 303.1232. Found: 303.1231.

Example 13

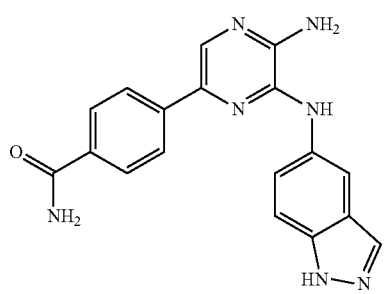 [SMILES: NC(=O)c1ccc(-c2cnc(N)c(Nc3ccc4[nH]ncc4c3)n2)cc1]

4-[5-Amino-6-(1H-indazol-5-ylamino)pyrazin-2-yl]benzamide, trifluoroacetate

Using procedure B: 5-Bromo-N3-(1H-indazol-5-yl)-pyrazine-2,3-diamine (15 mg) and 4-benzamide boronic acid (12 mg) yielded 1.5 mg of the title compound. HRMS calcd for $C_{18}H_{15}N_7O$: 345.1338. Found: 345.1335.

Example 14

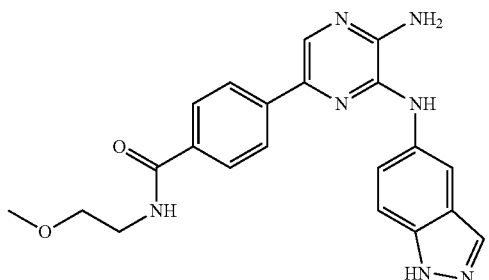

4-[5-Amino-6-(1H-indazol-5-ylamino)pyrazin-2-yl]-N-(2-methoxyethyl)benzamide, trifluoroacetate Using procedure B: 5-Bromo-N3-(1H-indazol-5-yl)-pyrazine-2,3-diamine (15 mg) and [4-[[(2-methoxyethyl)amino]carbonyl]phenyl]boronic acid (16 mg) yielded 2.5 mg of the title compound. HRMS calcd for $C_{21}H_{21}N_7O_2$: 403.1757. Found: 403.1751.

Intermediate 5

5-Bromo-N3-[2-(1H-indol-3-yl)ethyl]-pyrazine-2,3-diamine

Using procedure A: 2-Amino-3,5-dibromo-pyrazine (300 mg) and tryptamine (570 mg) yielded 600 mg of a 1:1 mixture of tryptamine and the desired product MS m/z 333 [M+H]+ which was used without further purification or characterization.

Example 15

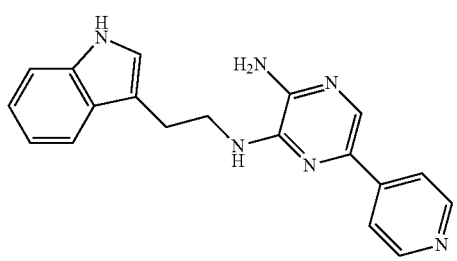 [SMILES: Nc1ncc(-c2ccncc2)nc1NCCc1c[nH]c2ccccc12]

N3-[2-(1H-Indol-3-yl)ethyl]-5-pyridin-4-ylpyrazine-2,3-diamine, trifluoroacetate Using procedure B: 5-Bromo-N3-[2-(1H-indol-3-yl)ethyl]-pyrazine-2,3-diamine (25 mg) and 4-pyridinyl boronic acid (14 mg) yielded 2.4 mg of the title compound. HRMS calcd for $C_{19}H_{18}N_6$: 330.1593. Found: 330.1602 $^1$H NMR (400 MHz, CD$_3$OD) δ ppm 3.20 (t, J=7 Hz, 2H) 3.95 (t, J=7 Hz, 2H) 6.92-7.19 (m, 3H) 7.32 (d, J=8 Hz, 1H) 7.58 (d, J=8 Hz, 1H) 8.18 (s, 1H) 8.41 (d, J=6 Hz, 2H) 8.62 (d, J=6 Hz, 2H).

Example 16

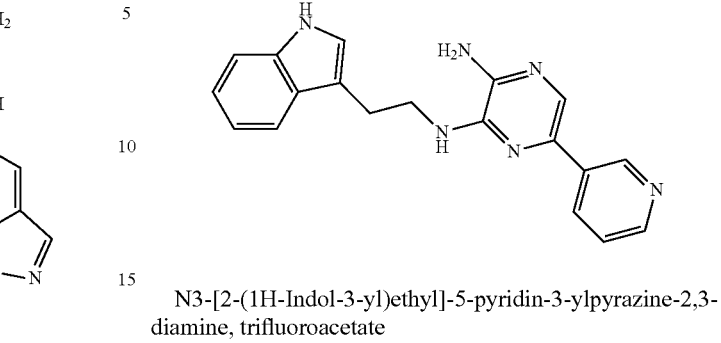

N3-[2-(1H-Indol-3-yl)ethyl]-5-pyridin-3-ylpyrazine-2,3-diamine, trifluoroacetate Using procedure B: 5-Bromo-N3-[2-(1H-indol-3-yl)ethyl]-pyrazine-2,3-diamine (25 mg) and 3-pyridinyl boronic acid (14 mg) yielded 2.7 mg of the title compound. HRMS calcd for $C_{19}H_{18}N_6$: 330.1593. Found: 330.1602. $^1$H NMR (400 MHz, CD$_3$OD) δ ppm 3.20 (t, J=7 Hz, 2H) 3.99 (t, J=7 Hz, 2H) 6.94-7.18 (m, 3H) 7.30 (d, J=8 Hz, 1H) 7.58 (d, J=7 Hz, 1H) 7.80 (s, 1H) 7.83-7.94 (m, 1H) 8.66 (d, J=5 Hz, 1H) 8.77 (d, J=8 Hz, 1H) 9.14 (s, 1H).

Example 17

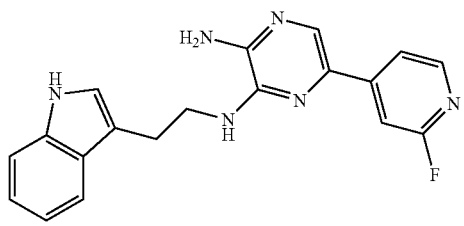 [SMILES: Nc1ncc(-c2ccnc(F)c2)nc1NCCc1c[nH]c2ccccc12]

5-(2-Fluoropyridin-4-yl)-N3-[2-(1H-indol-3-yl)ethyl]pyrazine-2,3-diamine, trifluoroacetate Using procedure B: 5-Bromo-N3-[2-(1H-indol-3-yl)ethyl]-pyrazine-2,3-diamine (25 mg) and 2-fluoro-4-pyridinyl boronic acid (16 mg) yielded 3.1 mg of the title compound. HRMS calcd for $C_{19}H_{17}FN_6$: 348.1499. Found: 348.1505. $^1$H NMR (400 MHz, CD$_3$OD) δ ppm 3.21 (t, J=7 Hz, 2H) 3.99 (t, J=7 Hz, 2H) 6.92-7.20 (m, 3H) 7.33 (d, J=8 Hz, 1H) 7.57 (d, J=7 Hz, 1H) 7.79 (s, 1H) 8.14 (dd, J=7, 5 Hz, 1H) 8.46 (d, J=5 Hz, 1H) 8.59 (d, J=4 Hz, 1H).

Example 18

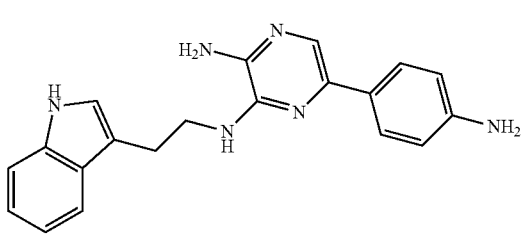 [SMILES: Nc1ccc(-c2cnc(N)c(NCCc3c[nH]c4ccccc34)n2)cc1]

5-(4-Aminophenyl)-N3-[2-(1H-indol-3-yl)ethyl]pyrazine-2,3-diamine, trifluoroacetate Using procedure B: 5-Bromo-N3-[2-(1H-indol-3-yl)ethyl]-pyrazine-2,3-diamine (25 mg) and 4-aminophenyl boronic acid (15 mg) yielded 4.4 mg of the title compound. HRMS calcd for $C_{20}H_{20}N_6$: 344.1749. Found: 344.1748. $^1$H NMR (400 MHz, CD$_3$OD) δ ppm 3.22 (t, J=7 Hz, 2H) 3.98 (t, J=7 Hz, 2H) 6.94-7.05 (m, 1H) 7.08-7.16 (m, 2H) 7.17-7.25 (m, 2H) 7.35 (d, J=8 Hz, 1H) 7.51 (s, 1H) 7.58 (d, J=7 Hz, 1H) 7.87-8.03 (m, 2H).

Example 19

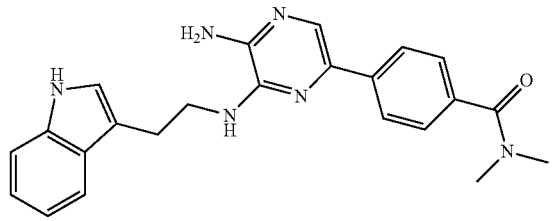 [SMILES: CN(C)C(=O)c1ccc(-c2cnc(N)c(NCCc3c[nH]c4ccccc34)n2)cc1]

4-(5-Amino-6-{[2-(1H-indol-3-yl)ethyl]amino}pyrazin-2-yl)-N,N-dimethylbenzamide, trifluoroacetate Using procedure B: 5-Bromo-N3-[2-(1H-indol-3-yl)ethyl]-pyrazine-2,3-diamine (25 mg) and 4-N,N-dimethylbenzamide boronic acid (22 mg) yielded 3.0 mg of the title compound. MS m/z 437 [M+H]$^+$. $^1$H NMR (400 MHz, CD$_3$OD) δ 3.06 (s, 3H) 3.15 (s, 3H) 3.22 (t, J=7 Hz, 2H) 3.99 (t, J=7 Hz, 2H) 6.96-7.05 (m, 1H) 7.06-7.16 (m, 2H) 7.34 (d, J=8 Hz, 1H) 7.48-7.55 (m, 2H) 7.58 (d, J=7 Hz, 1H) 7.61 (s, 1H) 7.96-8.05 (m, 2H).

Example 20

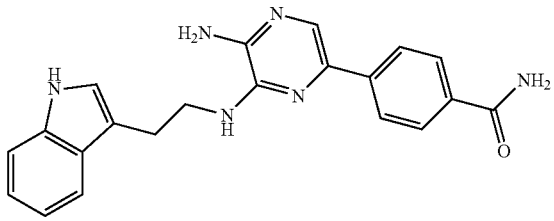 [SMILES: NC(=O)c1ccc(-c2cnc(N)c(NCCc3c[nH]c4ccccc34)n2)cc1]

4-(5-Amino-6-{[2-(1H-indol-3-yl)ethyl]amino}pyrazin-2-yl)benzamide, trifluoroacetate Using procedure B: 5-Bromo-N3-[2-(1H-indol-3-yl)ethyl]-pyrazine-2,3-diamine (25 mg) and 4-benzamide boronic acid (19 mg) yielded 4.8 mg of the title compound. HRMS calcd for $C_{21}H_{20}N_6O$: 372.1699. Found: 372.1696. $^1$H NMR (400 MHz, CD$_3$OD) δ 3.23 (t, J=7 Hz, 2H) 3.99 (t, J=7 Hz, 2H) 7.02 (t, J=7 Hz, 1H) 7.07-7.17 (m, 2H) 7.35 (d, J=8 Hz, 1H) 7.58 (d, J=8 Hz, 1H) 7.64 (s, 1H) 7.94-8.00 (m, 2H) 8.00-8.08 (m, 2H).

Example 21

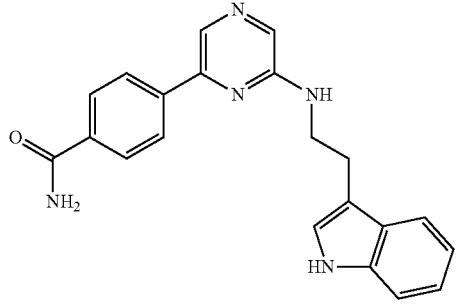 [SMILES: NC(=O)c1ccc(-c2cncc(NCCc3c[nH]c4ccccc34)n2)cc1]

4-(6-{[2-(1H-Indol-3-yl)ethyl]amino}pyrazin-2-yl)benzamide, trifluoroacetate Tryptamine (100 mg), 2,6-dichloropyrazine (100 mg) and triethylamine (135 mg) were mixed in 4 mL acetonitrile and heated to 150° C. for 1 h. Aqueous saturated NaHCO$_3$ and dichloromethane were added to the reaction mixture and the phases were separated. The water phase was extracted with dichloromethane. The combined organic phases were washed with brine and concentrated. The crude intermediate, 6-chloro-N-[2-(1H-indol-3-yl)ethyl]pyrazin-2-amine, (4-aminocarbonylphenyl)boronic acid (121 mg), K$_2$CO$_3$ (275 mg) and Pd(tetrakis(triphenylphosphine)) (38 mg) were dissolved in 4 mL dioxane and 1 mL H$_2$O and the reaction mixture was heated to 100° C. over night. 1M NaOH$_{(aq)}$ and dichloromethane were added to the mixture and the phases separated. The water phase was extracted with dichloromethane. The combined organic phases were washed with brine and concentrated. The crude product was purified by preparative HPLC (ACE C8 column; mobile phase: 0.1% TFA-CH$_3$CN) to give the title compound (85 mg) as a white solid in the form of its corresponding trifluoroacetate salt. HRMS calcd for $C_{21}H_{19}N_5O$: 357.1590. Found: 357.1585. $^1$H NMR (400 MHz, DMSO-d$_6$) δ 3.03 (t, J=7 Hz, 2H) 3.68 (t, J=7 Hz, 2H) 6.99-7.01 (m, 1H) 7.05-7.15 (m, 1H) 7.22 (d, J=2 Hz, 1H) 7.36 (d, J=8 Hz, 1H) 7.44 (s, 1H) 7.62 (d, J=7 Hz, 1H) 7.94 (s, 1H) 7.98 (d, J=8 Hz, 2H) 8.14 (d, J=8 Hz, 2H) 8.33 (s, 1H) 10.84 (s, 1H).

Example 22

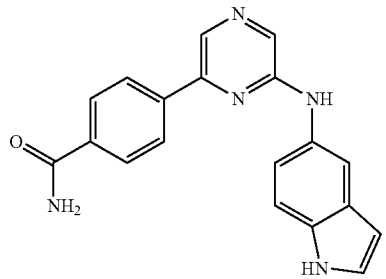 [SMILES: NC(=O)c1ccc(-c2cncc(Nc3ccc4[nH]ccc4c3)n2)cc1]

4-[6-(1H-Indol-5-ylamino)pyrazin-2-yl]benzamide, trifluoroacetate

5-Aminoindole (100 mg), 2,6-dichloropyrazine (100 mg) and triethylamine (135 mg) were mixed in 4 mL acetonitrile and heated to 150° C. for 1 h. Aqueous saturated NaHCO₃ and dichloromethane were added to the reaction mixture and the phases were separated. The water phase was extracted with dichloromethane. The combined organic phases were washed with brine and concentrated. The crude intermediate, 6-chloro-N-(1H-indol-5-yl)pyrazin-2-amine, (4-aminocarbonylphenyl)boronic acid (121 mg), K₂CO₃ (275 mg) and Pd(tetrakis(triphenylphosphine)) (38 mg) were dissolved in 4 mL dioxane and 1 mL H₂O and the reaction mixture was heated to 100° C. over night. 1M NaOH$_{(aq)}$ and dichloromethane were added to the mixture and the phases separated. The water phase was extracted with dichloromethane. The combined organic phases were washed with brine and concentrated. The crude product was purified by preparative HPLC (ACE C8 column; mobile phase: 0.1% TFA-CH₃CN) to give the title compound (85 mg) as a white solid in the form of its corresponding trifluoroacetate salt. HRMS calcd for C₁₉H₁₅N₅O: 329.1277. Found: 329.1279. ¹H NMR (400 MHz, CD₃OD) δ 7.27 (d, J=3.01 Hz, 1H) 7.31-7.37 (m, 1H) 7.40-7.43 (m, 1H) 7.47-7.51 (m, 1H) 7.85-7.93 (m, 1H) 7.95-8.08 (m, 3H) 8.19-8.26 (m, 2H) 8.38 (s, 1H).

Example 23

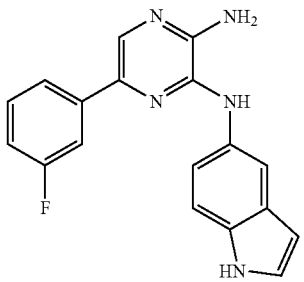 [SMILES: Nc1ncc(-c2cccc(F)c2)nc1Nc1ccc2[nH]ccc2c1]

5-(3-fluorophenyl)-N~3~-1H-indol-5-ylpyrazine-2,3-diamine. Was acquired from BioFocus DPI: HRMS calcd for C18H14FN5: 319.123324. Found mass: 319.123684. MS m/z 320 [M+H]⁺.

Example 24

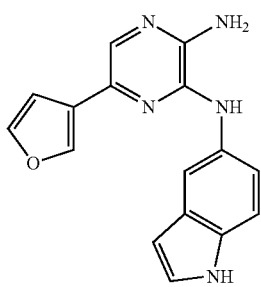 [SMILES: Nc1ncc(-c2ccoc2)nc1Nc1ccc2[nH]ccc2c1]

5-(3-furyl)-N~3~-1H-indol-5-ylpyrazine-2,3-diamine. Was acquired from BioFocus DPI: HRMS calcd for C16H13N5O: 291.112010. Found mass: 291.112130. MS m/z 292 [M+H]⁺.

Example 25

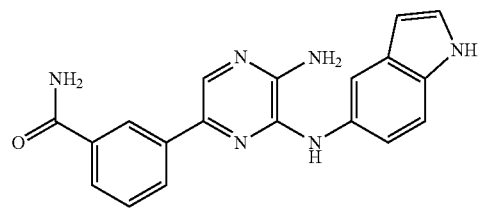 [SMILES: NC(=O)c1cccc(-c2cnc(N)c(Nc3ccc4[nH]ccc4c3)n2)c1]

3-[5-amino-6-(1H-indol-5-ylamino)pyrazin-2-yl]benzamide. Was acquired from BioFocus DPI: HRMS calcd for C19H16N6O: 344.138559. Found mass: 344.138509. MS m/z 345 [M+H]⁺.

Example 26

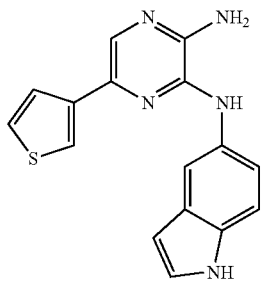 [SMILES: Nc1ncc(-c2ccsc2)nc1Nc1ccc2[nH]ccc2c1]

N~3~-1H-indol-5-yl-5-(3-thienyl)pyrazine-2,3-diamine. Was acquired from BioFocus DPI: HRMS calcd for C16H13N5S: 307.089166. Found mass: 307.089106. MS m/z 308 [M+H]⁺.

Example 27

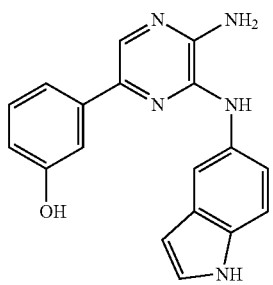 [SMILES: Nc1ncc(-c2cccc(O)c2)nc1Nc1ccc2[nH]ccc2c1]

3-[5-amino-6-(1H-indol-5-ylamino)pyrazin-2-yl]phenol. Was acquired from BioFocus DPI: HRMS calcd for C18H15N5O: 317.127660. Found mass: 317.127990. MS m/z 318 [M+H]⁺.

Example 28

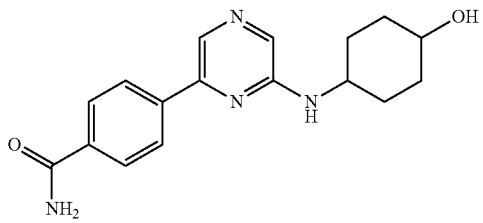 [SMILES: NC(=O)c1ccc(-c2cncc(NC3CCC(O)CC3)n2)cc1]

4-{6-[(trans-4-Hydroxycyclohexyl)amino]pyrazin-2-yl}benzamide, trifluoroacetate 2,6-Dichloropyrazine (500 mg), trans-4-amino-cyclohexanol (380 mg) and triethylamine (500 mg) were dissolved in 4 mL acetonitrile/1 mL water and the reaction mixture was heated to 150° C. for 15 min. Water and dichloromethane were added to the mixture and the phases were separated. The water phase was extracted once more with dichloromethane. The combined organic phases were washed (water and brine) and evaporated to yield 750 mg of intermediate 6-chloro-N-(trans-4-hydroxycyclohexyl)pyrazin-2-amine with 85% purity. A portion of this material (30 mg), potassium carbonate (55 mg), 4-benzamide boronic acid (26 mg) and Pd(tetrakis(triphenylphosphine)) (5 mg) were dissolved in 4 mL dioxane and 1 mL $H_2O$ and the reaction mixture was heated to 100° C. over night. 1M $NaOH_{(aq)}$ and dichloromethane were added to the mixture and the phases separated. The water phase was extracted with dichloromethane. The combined organic phases were washed with brine and concentrated. The crude product was purified by preparative HPLC (ACE C8 column; mobile phase: 0.1% TFA-$CH_3CN$) to give the title compound (5.0 mg) as a white solid in the form of its corresponding trifluoroacetate salt. HRMS calcd for $C_{17}H_{20}N_4O_2$: 312.1586. Found: 312.1585.

Example 29

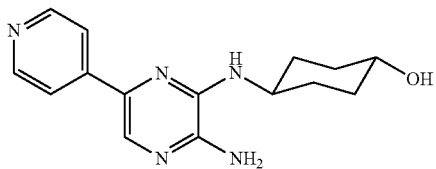 [SMILES: Nc1ncc(-c2ccncc2)nc1NC1CCC(O)CC1]

trans-4-[(3-Amino-6-pyridin-4-ylpyrazin-2-yl)amino]cyclohexanol

A suspension of 2,6-dibromo-3-aminopyrazine (6.44 g, 0.0255 mol), $K_2CO_3$ (6.9 g, 0.05 mol) and trans-4-amino-cyclohexanol (HCl salt) (7.55 g, 0.05 mol) in $H_2O$ (10.0 mL) was heated under reflux for 72 h (a homogenous solution is rapidly formed and after ca 30 h a solid is slowly precipitated. The mixture was cooled and the insoluble solid collected and washed with water to afford 4.336 g (59%) of intermediate trans-4-[(3-amino-6-bromopyrazin-2-yl)amino]cyclohexanol. To a solution of the crude material (4.336 g, 0.0151 mol), 4-pyridylboronic acid (1.84 g, 0.0151 mol) tetrakis(triphenylphosphine)palladium(0) (870 mg, 0.7 mmol; 5 mol %) in PhMe (200 mL) were added aqueous 2M sodium carbonate (40 ml), and ethanol (40 mL). The mixture was heated at reflux overnight. The mixture was concentrated by evaporation and an insoluble dark coloured solid collected by filtration. This material was then dissolved in MeOH and flash chromatographed over silica EtOAc-MeOH (9:1) to give a pale yellow solid (2.2 g). Further elution with EtOAc-MeOH (7:1) gave an additional crop of pale yellow solid (930 mg) which was quite heavily contaminated with silica. Both crops of solid were combined and purified by preparative HPLC (ACE C8 column; mobile phase: 0.1% TFA-$CH_3CN$) to afford 2.2 g of the title product. HPLC purity 100%; $^1$H NMR (400 MHz, DMSO-$d_6$) δ ppm 1.33-1.40 (m, 4H), 1.89-1.92 (m, 2H), 2.01-2.04 (m, 2H), 3.47-3.49 (m, 1H), 3.93-3.97 (m, 1H), 8.29 (s, 1H), 8.41 (d, 2H, J=5.0 Hz), 8.80 (d, 2H, J=5.0 Hz); MS (API-ES/Positive); m/z: 286 (M+H)$^+$.

Example 30

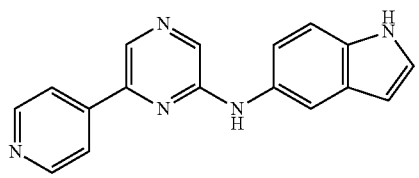 [SMILES: c1cc(-c2cncc(Nc3ccc4[nH]ccc4c3)n2)ccn1]

N-(6-Pyridin-4-ylpyrazin-2-yl)-1H-indol-5-amine

A mixture of 2,6-dichloropyrazine (0.845 g, 5.67 mmol), 5-aminoindole (0.5 g, 3.78 mmol), BINAP (0.051 g, 0.0831 mmol), sodium tertiary butoxide (0.51 g, 5.29 mmol) and palladium acetate (0.0186 g, 0.0831 mmol) in toluene (25 mL) was heated at 85° C. for 22 h under nitrogen. $CH_2Cl_2$ was added, the reaction mixture was filtered through Celite, and the solvent was evaporated. The residue was purified by column chromatography (5% methanol in $CH_2Cl_2$ as eluent) to give 0.180 g (13%) of intermediate N-(6-chloro-pyrazin-2-yl)-1H-indol-5-amine. $^1$H NMR (CD$_3$OD) δ 7.97 (s, 1H), 7.84 (s, 1H), 7.77 (s, 1H), 7.42-7.39 (d, J=8.63 Hz, 1H), 7.28-7.20 (m, 2H), 6.47-6.46 (d, J=2.83 Hz, 1H); MS (API-ES/Positive); m/z: 245 (M+H)$^+$.

A mixture of N-(6-chloro-pyrazin-2-yl)-1H-indol-5-amine (0.030 g, 0.123 mmol), pyridine-4-boronic acid (0.018 g, 0.147 mmol), sodium carbonate (0.067 g, 0.615 mmol) and tetrakis(triphenylphosphine)palladium(0) (0.007 g, 0.006 mmol) in DME:water (3:2, 5 mL) was heated at reflux for 20 h. The reaction mixture was concentrated under reduced pressure and the residue obtained was extracted with dichloromethane. The organic layer was washed with water, brine, dried over sodium sulfate and concentrated. The crude product was purified by flash chromatography (5% methanol in $CH_2Cl_2$ as eluent) to yield N-(6-pyridin-4-ylpyrazin-2-yl)-1H-indol-5-amine (0.011 g, 31%) as a yellow solid. $^1$H NMR (CD$_3$OD) δ 8.70-8.68 (d, J=6.17 Hz, 2H), 8.47 (s, 1H), 8.15 (s, 1H), 8.14 (d, J=1.50 Hz, 2H) 7.96 (d, J=1.70 Hz, 1H), 7.45-7.43 (d, J=8.64 Hz, 1H), 7.37-7.35 (dd, J=10.46, 1.83 Hz, 1H), 7.29-7.28 (d, J=3.06 Hz, 1H), 6.49-6.48 (d, J=3.02 Hz, 1H); MS (API-ES/Positive); m/z: 288 (M+H)$^+$.

Example 31

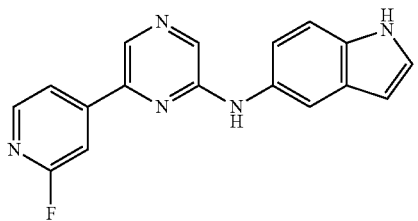 [SMILES: Fc1cc(-c2cncc(Nc3ccc4[nH]ccc4c3)n2)ccn1]

N-[6-(2-Fluoropyridin-4-yl)pyrazin-2-yl]-1H-indol-5-amine

A mixture of N-(6-chloro-pyrazin-2-yl)-1H-indol-5-amine (0.05 g, 0.205 mmol), 2-fluoropyridine-4-boronic acid (0.057 g, 0.4 mmol), sodium carbonate (0.112 g, 1.025 mmol) and tetrakis(triphenylphosphine)palladium(0) (0.012 g, 0.01 mmol) in DME:water (3:2, 3 mL) was heated at reflux for 20 h. The reaction mixture was concentrated under reduced pressure and the residue obtained was extracted with dichloromethane. The organic layer was washed with water, brine, dried over sodium sulfate and concentrated. The crude product was purified by flash chromatography (5% methanol in $CH_2Cl_2$ as eluent) to yield the title compound (0.015 g, 24%) as a yellow solid. $^1$H NMR ($CD_3OD$) δ 8.47 (s, 1H), 8.35-8.33 (d, J=5.29 Hz, 1H), 8.16 (s, 1H), 8.01-8.00 (d, J=5.13 Hz, 1H), 7.94 (s, 1H), 7.78 (s, 1H), 7.45-7.43 (d, J=8.64 Hz, 1H), 7.35-7.33 (dd, J=10.33, 1.72 Hz, 1H), 7.29 (d, J=2.95 Hz, 1H), 6.48-6.47 (d, J=2.58 Hz, 1H); MS (API-ES/Positive); m/z: 306 (M+H)$^+$.

Example 32

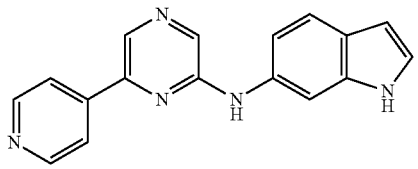 [SMILES: c1cc(-c2cncc(Nc3ccc4cc[nH]c4c3)n2)ccn1]

N-(6-Pyridin-4-ylpyrazin-2-yl)-1H-indol-6-amine

A mixture of 2,6-dichloropyrazine (0.150 g, 1.006 mmol), 6-aminoindole (0.200 g, 1.51 mmol), BINAP (0.0137 g, 0.02215 mmol), sodium tertiary butoxide (0.136 g, 1.409 mmol) and palladium acetate (0.005 g, 0.02215 mmol) in toluene (8 mL) was heated at 85° C. for 16 h under nitrogen. $CH_2Cl_2$ was added, the reaction mixture was filtered through Celite, and the solvent was evaporated. The residue was purified by column chromatography (5% methanol in $CH_2Cl_2$ as eluent) to give 0.070 g (33%) of intermediate (6-chloropyrazin-2-yl)-(1H-indol-6-yl)-amine. $^1$H NMR (CDCl$_3$) δ 8.36 (brs, 1H, NH), 8.08 (s, 1H), 7.92 (s, 1H), 7.64-7.59 (m, 2H), 7.23 (s, 1H), 7.01-6.98 (d, J=8.37 Hz, 1H), 6.87 (s, 1H, NH), 6.56 (s, 1H); MS (API-ES/Positive); m/z: 245 (M+H)$^+$.

A mixture of (6-chloro-pyrazin-2-yl)-(1H-indol-6-yl)-amine (0.070 g, 0.2868 mmol), pyridine-4-boronic acid (0.042 g, 0.344 mmol), sodium carbonate (0.150 g, 1.43 mmol) and tetrakis(triphenylphosphine)palladium(0) (0.0165 g, 0.0143 mmol) in DME:water (3:2, 5 mL) was heated at reflux for 20 h. The reaction mixture was concentrated under reduced pressure and the residue obtained was extracted with dichloromethane. The organic layer was washed with water, brine, dried over sodium sulfate and concentrated. The crude product was purified by flash chromatography (5% methanol in $CH_2Cl_2$ as eluent) to yield N-(6-pyridin-4-ylpyrazin-2-yl)-1H-indol-6-amine (0.030 g, 36.5%) as a yellow solid. $^1$H NMR (CD$_3$OD) δ 8.73-8.72 (d, J=5.68 Hz, 2H), 8.51 (s, 1H), 8.23-8.20 (m, 4H), 7.56-7.54 (d, J=8.46 Hz, 1H), 7.22 (d, J=2.99 Hz, 1H), 7.14 (dd, J=10.18, 1.74 Hz, 1H), 6.45 (d, J=2.75 Hz, 1H); MS (API-ES/Positive); m/z: 288 (M+H)$^+$.

Example 33

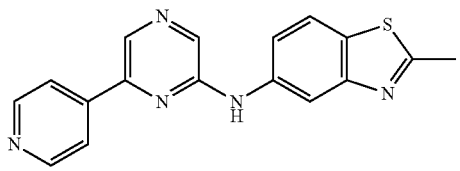 [SMILES: Cc1nc2cc(Nc3cncc(-c4ccncc4)n3)ccc2s1]

2-Methyl-N-(6-pyridin-4-ylpyrazin-2-yl)-1,3-benzothiazol-5-amine

A mixture of 2,6-dichloropyrazine (0.150 g, 1.006 mmol), 5-amino-2-methylbenzothiazole (0.250 g, 1.51 mmol), BINAP (0.0137 g, 0.02215 mmol), sodium tertiary butoxide (0.136 g, 1.409 mmol) and palladium acetate (0.005 g, 0.02215 mmol) in toluene (8 mL) was heated at 85° C. for 16 h under nitrogen. $CH_2Cl_2$ was added, the reaction mixture was filtered through Celite, and the solvent was evaporated. The residue was purified by column chromatography (5% methanol in $CH_2Cl_2$ as eluent) to give 0.180 g (65%) of intermediate (6-chloro-pyrazin-2-yl)-(2-methyl-benzothiazol-5-yl)-amine. $^1$H NMR (CDCl$_3$) δ 7.59-7.54 (d, J=15.6 Hz, 2H), 7.38 (s, 1H), 7.19-7.16 (d, J=8.65 Hz, 1H), 6.98-6.95 (d, J=8.41 Hz, 1H), 6.71 (brs, 1H, NH), 2.31 (s, 3H, CH$_3$); MS (API-ES/Positive); m/z: 277 (M+H)$^+$. A mixture of (6-chloro-pyrazin-2-yl)-(2-methyl-benzothiazol-5-yl)-amine (0.075 g, 0.271 mmol), pyridine-4-boronic acid (0.040 g, 0.326 mmol), sodium carbonate (0.143 g, 1.35 mmol) and tetrakis(triphenylphosphine)palladium(0) (0.0156 g, 0.0135 mmol) in DME:water (3:2, 5 mL) was heated at reflux for 20 h. The reaction mixture was concentrated under reduced pressure and the residue obtained was extracted with dichloromethane. The organic layer was washed with water, brine, dried over sodium sulfate and concentrated. The crude product was purified by flash chromatography (5% methanol in $CH_2Cl_2$ as eluent) to yield 2-methyl-N-(6-pyridin-4-ylpyrazin-2-yl)-1,3-benzothiazol-5-amine (0.075 g, 86.5%) as a yellow solid. $^1$H NMR (CD$_3$OD) δ 8.82 (m, 3H), 8.72 (s, 1H), 8.45-8.44 (m, 2H), 8.35 (s, 1H), 7.92-7.90 (d, J=8.67 Hz, 1H), 7.61-7.59 (dd, J=10.63, 1.94 Hz, 1H), 2.89 (s, 3H, CH$_3$); MS (API-ES/Positive); m/z: 320 (M+H)$^+$.

Example 34

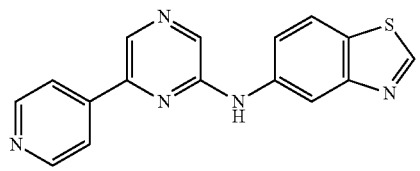 [SMILES: c1cc(-c2cncc(Nc3ccc4scnc4c3)n2)ccn1]

N-(6-Pyridin-4-ylpyrazin-2-yl)-1,3-benzothiazol-5-amine

A mixture of 2,6-dichloropyrazine (0.150 g, 1.006 mmol), 5-amino-benzothiazole (0.151 g, 1.006 mmol), BINAP (0.0137 g, 0.02215 mmol), sodium tertiary butoxide (0.136 g, 1.409 mmol) and palladium acetate (0.005 g, 0.02215 mmol) in toluene (8 mL) was heated at 85° C. for 16 h under nitrogen. $CH_2Cl_2$ was added, the reaction mixture was filtered through Celite, and the solvent was evaporated. The residue was purified by column chromatography (5% methanol in $CH_2Cl_2$ as eluent) to give 0.140 g (53%) of intermediate benzothiazol-5-yl-(6-chloro-pyrazin-2-yl)-amine. $^1$H NMR (CDCl$_3$) δ 10.12 (s, 1H), 9.38 (s, 1H), 8.59 (s, 1H), 8.22 (s, 1H), 8.11-8.08 (d, J=8.67 Hz, 1H), 8.02 (s, 1H), 7.6-7.57 (d, J=8.67 Hz, 1H); MS (API-ES/Positive); m/z: 263 (M+H)$^+$.

A mixture of benzothiazol-5-yl-(6-chloro-pyrazin-2-yl)-amine (0.06 g, 0.228 mmol), pyridine-4-boronic acid (0.043 g, 0.342 mmol), sodium carbonate (0.124 g, 1.14 mmol) and tetrakis(triphenylphosphine)palladium(0) (0.013 g, 0.0114 mmol) in DME:water (3:2, 5 mL) was heated at reflux for 22 h. The reaction mixture was concentrated under reduced pressure and the residue obtained was extracted with dichloromethane. The organic layer was washed with water, brine, dried over sodium sulfate and concentrated. The crude product was purified by flash chromatography (5% methanol in $CH_2Cl_2$ as eluent) to yield N-(6-pyridin-4-ylpyrazin-2-yl)-1,3-benzothiazol-5-amine (0.035 g, 50%) as a yellow solid. $^1$H NMR (CD$_3$OD) δ 9.31 (s, 1H), 8.98 (d, J=2.02 Hz, 1H), 8.75-8.74 (d, J=5.31 Hz, 2H), 8.64 (s, 1H), 8.31 (s, 1H), 8.24-8.22 (d, J=5.99 Hz, 2H), 8.06-8.04 (d, J=8.77 Hz, 1H), 7.74-7.71 (dd, J=10.73, 2.01 Hz, 1H); MS (API-ES/Positive); m/z: 306 (M+H)$^+$.

Biological Methods

The ability of a compound of the invention to inhibit FLT3 can be determined using in vitro and in vivo assays known in the art. Several in vitro kinase assays for FLT3 inhibition have been described in the literature using cloned kinase domain and measuring phosphorylation of a substrate peptide. In addition, cell-lines expressing FLT3 have been used to measure the effect on viability and proliferation in a cellular assay.

Enzyme Inhibition Assay

The compounds according to the invention were evaluated for their inhibition of FLT3 by the following method:

In Vitro FLT3 Kinase Assay

An enzyme inhibition assay for the tyrosine kinase domain of FLT3 was established using a fluorescence polarization technique, Immobilized Metal Ion Affinity-Based Fluorescence Polarization (IMAP) from Molecular Devices.

Briefly: kinase activity is measured by incubating a fluorescent peptide substrate with the kinase domain. After completion of the kinase reaction a binding buffer is added. Upon phosphorylation of the substrate, the fluorescent peptide gains the ability to bind to a metal-coated nanoparticle. When the substrate is bound to the nanoparticle, the rotational is speed of the peptide is reduced, and thus the fluorescence polarization (fp) becomes high. Compounds inhibiting the kinase activity of the enzyme will result in a low degree of phosphorylated substrate and a low fp-signal.

Reagents

IMAP Buffer kit with Progressive Binding System (Molecular Devices, #R8124): Reaction buffer: 10 mM Tris-HCL pH 7.2 with 10 mM MgCl2, 0.05% NaN3 and 0.01% Tween 20. Prior to use DTT was added to 1 mM DTT final concentration (complete reaction buffer).

Binding solution was prepared from buffer kit according to the manufactures recommendations. Binding Reagent was diluted 1:1500 in 40% Binding buffer A and 60% Binding buffer B.

FLT3 enzyme used was recombinant human FLT3 from Upstate (#14-500) 7.2 U/ml, N-terminal GST tagged, amino acids 564-end.

Substrate peptide used: FAM-CSKtide from Molecular Devices (#R7269) 20 µM, 5FAM-KKKKEEIYFFFG-NH2.

ATP stock solution 10 mM

DTT stock solution 100 mM

Compound dilutions: 0.01% Tween20+1% DMSO in reaction buffer. Reagents were diluted in complete reaction buffer to working solutions.

Assay Conditions

Final concentrations:

Flt3: 0.0125 U/ml (batch dependent)

FAM-CSKtide: 100 nM

ATP: 100 µM

Compound dose response: eleven step dilution 1:3, concentration range 25000-0.42 nM, 5000-0.085 nM, resp. 500-0.0085 nM depending of the potency of compound.

Protocol

I. Set up kinase reaction in 20 µl volume for 1 h:
   Pipette into 96-well black ½ area plate:
   5 µl compound dilution or vehicle
   5 µl substrate peptide (400 nM)
   5 µl enzyme (0.05 U/ml) or complete reaction buffer for non specific background (NSB)
   5 µl ATP (400 µM)
   Cover the plate and incubate at room temperature with gentle agitation II. Binding incubation for 2 h (minimum time):
   Add 60 µl binding solution.
   Cover the plate and incubate at room temperature with gentle agitation III. Fluorescence Polarization analysis:
   Measure fluorescein using a plate reader (Analyst AD) excitation wave length 485 and emission wave length 530, reading with integration time of 0.1 sec. (Alternatively Victor$^2$ V Wallac 485/535 nm)

Stock concentrations of test compounds were made at 10 mM in 100% DMSO. In the assay, compounds were tested in single point at 10 and 1 micromolar, diluted in reaction buffer as described above. Compounds with an inhibitory activity greater than 60% inhibition at 1 micromolar were subsequently tested in dose-respons for IC$_{50}$ determinations, using an eleven point dilution range with 1:3 dilution steps (typically from 25000 nM to 0.42 nM, more potent compounds were assayed from 500 nM to 0.0085 nM). IC$_{50}$ values were obtained by the equation (A+4B−A)/(1+((C/x)^D)))) where A equals min, B equals max, C equals IC$_{50}$ and D equals Hill slope.

The compounds in accordance with the invention can display IC$_{50}$ values between 1 nM and 2 µM (e.g. between 1 nM and 1 μM, between 1 nM and 500 nM, between 1 nM and 100 nM, between 1 nM and 25 nM, between 1 nM and 10 nM).
Cellular Assays AML cell-line MV4-11 carries the FLT3-internal tandem duplication. This cell-line has been widely used for evaluating the effect of FLT3-kinase inhibitors on viability and proliferation.

Briefly, cells are seeded at a low density into 96-well plates. Serial dilution of compounds is added and the cells are incubated for 72 hours. Total number of viable cells is measured using flow cytometry at the end of treatment, and the effect of the compounds is calculated as % inhibition compared to vehicle treated cells.
Cells and Culture Conditions All cells were cultured under standard cell culture conditions, at 37° Celsius in an atmosphere of 5% $CO_2$ in 90% humidity.

AML-cell line MV4-11 was cultured in DMEM Glutamax high glucose (4500 g/l glucose) supplemented with 10% Fetal Bovine Serum (FBS) from Invitrogen. Cells were subcultured twice weakly, growing to a density of approx 2 million cells per ml prior to subcultivation.
Viability and Proliferation Assay For viability determination, 3000-5000 cells were seeded in 50 microliter culture medium into a 96-well plate. Serial dilutions 1:3 of compounds from 10 mM DMSO stock were made in serumfree culture medium supplemented with penicillin and streptomycin. 50 microliter of the serial dilutions were added to the cell-suspension. The final concentration of compounds was from 5 micromolar to 0.8 nM, or from 500 nM to 0.08 nM respectively. The DMSO concentration was kept constant at 0.05%.

At the end of the treatment, 100 microliter viability reagent (Guava ViaCount) was added to each well and number of cells and viability was determined using flow cytometry (Guava 96-well ViaCount assay). Typically the vehicle treated (0.05% DMSO) cell-line cells had doubled three times during the experiment.

% Survival was calculated compared to the vehicle treated cells at the end of experiment. EC50 values were determined using the equation $(A+((B-A)/(1+((C/x)^D))))$ where A equals min, B equals max, C equals $EC_{50}$ and D equals Hill slope.
Results

TABLE 1

Typical mean $IC_{50}$ values (n = 4-8) determined in the FLT3 kinase assay.

| Example | IC50 (nM) |
|---------|-----------|
| 15 | 60 |
| 28 | 159 |
| 32 | 560 |

TABLE 2

$EC_{50}$ values determined in AML-cell line.

| Example | Cell data MV4-11 (nM) |
|---------|------------------------|
| 15 | 184 |
| 28 | 178 |
| 32 | 373 |

In Vitro Assay for Combinations of FLT3-Inhibitor and Chemotherapy

Sequence dependent synergistic activities of compounds of formula (I) and standard chemotherapy agents used in treating AML is performed as described in Brown et al. (2006) Leukemia 20: 1368-1376, and the results analysed using Calcusyn Software according to the principles of Chou and Talalay (1981) Eur J. Biochem.

The invention claimed is:

1. A compound which is N3-1H-indol-5-yl-5-pyridin-4-ylpyrazine-2,3-diamine, or a pharmacologically acceptable salt thereof.

2. A method for the treatment of acute myeloic leukemia (AML), said method comprising administering the compound of claim 1 to a human in need thereof.

* * * * *

UNITED STATES PATENT AND TRADEMARK OFFICE
CERTIFICATE OF CORRECTION

PATENT NO. : 8,436,171 B2  Page 1 of 1
APPLICATION NO. : 12/865359
DATED : May 7, 2013
INVENTOR(S) : Jensen et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 262 days.

Signed and Sealed this
Eighth Day of September, 2015

Michelle K. Lee
*Director of the United States Patent and Trademark Office*